United States Patent
Hamatake

(10) Patent No.: US 8,598,334 B2
(45) Date of Patent: Dec. 3, 2013

(54) HBV ANTISENSE INHIBITORS

(75) Inventor: Robert K. Hamatake, Durham, NC (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/502,370

(22) PCT Filed: Oct. 15, 2010

(86) PCT No.: PCT/US2010/052911
§ 371 (c)(1),
(2), (4) Date: Apr. 16, 2012

(87) PCT Pub. No.: WO2011/047312
PCT Pub. Date: Apr. 21, 2011

(65) Prior Publication Data
US 2012/0207709 A1    Aug. 16, 2012

Related U.S. Application Data

(60) Provisional application No. 61/252,380, filed on Oct. 16, 2009.

(51) Int. Cl.
*C07H 21/04* (2006.01)
*C12N 15/113* (2010.01)

(52) U.S. Cl.
USPC ........................ 536/24.5; 514/44 A

(58) Field of Classification Search
None
See application file for complete search history.

(56) References Cited

U.S. PATENT DOCUMENTS

| | | |
|---|---|---|
| 5,985,662 A | 11/1999 | Anderson et al. |
| 6,593,082 B1 | 7/2003 | Oon et al. |
| 2003/0032596 A1 | 2/2003 | Schneider et al. |
| 2003/0134808 A1* | 7/2003 | Wengel ............ 514/44 |
| 2003/0148985 A1 | 8/2003 | Morrissey et al. |
| 2003/0206887 A1 | 11/2003 | Morrissey et al. |
| 2004/0054156 A1* | 3/2004 | Draper et al. ......... 536/23.1 |
| 2005/0014712 A1 | 1/2005 | Hansen et al. |
| 2006/0128646 A1 | 6/2006 | Christensen et al. |
| 2008/0090843 A1 | 4/2008 | Schneider et al. |

FOREIGN PATENT DOCUMENTS

WO    2004/078181    9/2004

OTHER PUBLICATIONS

Iribarren, et al., 2'-O-Alkyl oligoribonucleotides as antisense probes, Proc. Natl Acad Sci 87: 7747-7751 (1990).
Supplementary European Search Report dated Mar. 14, 2013 for Application No. EP 10824199.3, Publication No. EP2512491.

* cited by examiner

*Primary Examiner* — Tracy Vivlemore
(74) *Attorney, Agent, or Firm* — Barbara J. Carter

(57) ABSTRACT

Antisense oligomers useful for modulating hepatitis B virus infections, and for the treatment of hepatitis B virus (HBV) and hepatitis B virus-related conditions in animals including humans. More particularly, antisense oligomers with modified nucleotides for treatment of HBV in animals, more particularly antisense oligomers comprising 2'O-4'C-methylene-bridged sugars, or nucleotides with other 2'O-4'C bridged sugars, also known as locked nucleic acids (LNA), for treatment of HBV in animals, and more particularly for treatment of HBV in humans.

35 Claims, 6 Drawing Sheets

HBV Patients with Compensated Disease:
HBeAg Positive

HBV Patients with Compensated Disease:
HBeAg Negative

*HBV Transcription*

Figure 6

| HBV genotype | Geographic area |
|---|---|
| A | Northwest Europe, North America, Central America |
| B | Indonesia, China, Vietnam |
| C | East Asia, Korea, China, Japan, Polynesia, Vietnam |
| D | Mediterranean area, Middle East, India |
| E | Africa |
| F | Native Americans, Polynesia |
| G | United States, France |
| H | Central America |

HBV ANTISENSE INHIBITORS

This application is filed pursuant to 35 U.S.C. §371 as a U.S. National Phase Application of International Patent Application Serial No. PCT/EP2010/052911 filed Oct. 15, 2010, which claims priority to U.S. Application No. 61/252,380 filed Oct. 16, 2009, the contents of which are incorporated herein by reference.

FIELD OF THE INVENTION

The present invention relates to antisense oligonucleotides useful for modulating gene expression and thereby treating disease, especially antisense oligomers for the treatment of hepatitis B virus (HBV) and hepatitis B virus-related conditions in animals including human. More particularly embodiments of the present invention relate to antisense oligomers with modified nucleosides for treatment of HBV in animals, more particularly antisense oligomers comprising nucleosides with 2'O-4'C-methylene-bridged sugars, and nucleosides with other bridged sugars as further described herein, also known as locked nucleic acids (LNA), for treatment of HBV in animals, and more particularly for treatment of HBV in humans.

BACKGROUND ART

Hepatitis B is a viral disease transmitted parenterally by contaminated material such as blood and blood products, contaminated needles, sexually and vertically from infected or carrier mothers to their offspring. In those areas of the world where the disease is common vertical transmission at an early age results in a high proportion of infected individuals becoming chronic carriers of hepatitis B. It is estimated by the World Health Organization that more than 2 billion people have been infected worldwide, with about 4 million acute cases per year, 1 million deaths per year, and 350-400 million chronic carriers. Approximately 25% of carriers die from chronic hepatitis, cirrhosis, or liver cancer and nearly 75% of chronic carriers are Asian. Hepatitis B virus is the second most significant carcinogen behind tobacco, causing from 60% to 80% of all primary liver cancer. HBV is 100 times more contagious than HIV.

Hepatitis B viral infections are a continuing medical problem because, like any rapidly-replicating infectious agent, there are continuing mutations that help some sub-populations of HBV become resistant to current treatment regimens. At the present time there are no effective therapeutic agents for treating humans infected with HBV infections which result in seroconversion to the virus in the body, or which effect a 90% reduction of antigen, compared to baseline numbers before treatment, in persons suffering from a hepatitis B viral infection. Currently the recommended therapies for chronic HBV infection by the American Association for the Study of Liver Diseases (AASLD) and the European Association for the Study of the Liver (EASL) include interferon alpha (INFα), pegylated interferon alpha-2a (Peg-IFN2a), entecavir, and tenofovir. However, typical interferon therapy is 48-weeks and results in serious and unpleasant side effects, and HBeAg seroconversion, 24 weeks after therapy has ceased, ranges from only 27-36%. Seroconversion of HBsAg is even lower—only 3% observed immediately after treatment ceases, with an increase to upwards of 12% after 5 years.

The nucleoside and nucleotide therapies entecavir and tenofovir are successful at reducing viral load, but the rates of HBeAg seroconversion and HBsAg loss are even lower than those obtained using IFNα therapy. Other similar therapies, including lamivudine (3TC), telbivudine (LdT), and adefovir are also used, but for nucleoside/nucleotide therapies in general, the emergence of resistance limits therapeutic efficacy.

Thus, there is a need in the art to discover and develop new anti-viral therapies. More particularly, there is a need for new anti-HBV therapies capable of increasing HBeAg and HBsAg seroconversion rates. These serum markers are indicative of immunological control of HBV infection and leads to an improved prognosis, i.e. prevention of liver disease and progression to cirrhosis, prevention of liver failure, prevention of hepatocellular cancer (HCC), prevention of liver disease—related transplantation, and prevention of death.

Recent clinical research has found a correlation between seroconversion and reductions in HBeAg (Fried et al (2008) Hepatology 47:428) and reductions in HBsAg (Moucari et al (2009) Hepatology 49:1151). Reductions in antigen levels may have allowed immunological control of HBV infection because high levels of antigens are thought to induce immunological tolerance. Current nucleoside therapies for HBV are capable of dramatic reductions in serum levels of HBV but have little impact on HBeAg and HBsAg levels. Antisense therapy differs from nucleoside therapy in that it can directly target the transcripts for the antigens and thereby reduce serum HBeAg and HBsAg levels. Because of the multiple, overlapping transcripts produced upon HBV infection, there is also an opportunity for a single antisense oligomer to reduce HBV DNA in addition to both HBeAg and HBsAg.

Antisense therapy is a form of treatment for genetic disorders or infections. When the genetic sequence of a particular gene is known to be causative of a particular disease, whether the gene is an original mammalian gene, an oncogene, or a gene from an infective organism, such as a gene from a bacterial species, a gene from a fungus, a gene from a parasite or a gene from a virus, it is possible to synthesize a strand of nucleic acid (DNA, RNA or a chemical analogue) that will bind to the messenger RNA (mRNA) produced by that gene and inactivate it, effectively turning that gene "off". This is because mRNA must be single stranded for it to be translated. Alternatively, the strand might be targeted to bind a splicing site on pre-mRNA and modify the exon content of an mRNA [1].

A DNA single strand sequence is often called the sense strand (or positive (+) sense strand) if an RNA version having the same sequence (except U in RNA for T in DNA) is translated or translatable into protein, and the complementary strand is called the antisense strand (or negative (−) sense strand).

Some regions within a double strand of DNA code for genes, which are usually instructions specifying the order of amino acids in an expressed, or translated, protein, together with regulatory sequences, splicing sites, noncoding introns and other regions. For a cell to express the protein coded by the DNA, one strand of the DNA serves as a template for the synthesis of a complementary strand of RNA. The template DNA strand is called the transcribed strand and its sequence is antisense, or complementary, to the mRNA transcript, which has the same sequence as the sense sequence of the original double-stranded DNA. Because the DNA is double-stranded, the strand complementary to the antisense sequence is called the non-transcribed strand, or sense strand, and has the same sequence as the mRNA transcript (except T nucleobases in the DNA sequence are substituted with U nucleobases in RNA sequence).

A nucleic acid that is complementary to the RNA transcribed from the DNA is termed an "anti-sense" oligonucleotide because its base sequence is complementary to the gene's messenger RNA (mRNA)—the "sense" sequence.

Thus, a coding DNA region having a sense sequence of 5'-AAGGTC-3" will be transcribed to produce a mRNA having a sense sequence of 5'-AAGGUC-3' and so an antisense oligomer to that sense sequence will have a sequence of 3'-UUCCAG-5' if it comprises RNA nucleobases, or 3'-TTC-CAG-5' if the antisense oligomer comprises DNA nucleobases.

Currently, a main focus of antisense therapy involves the use of an oligomer or oligonucleotide, approximately 20 nucleotide/nucleosides in length, synthesized to be complementary to the specific "sense" (5' to 3' orientation) DNA or mRNA sequence responsible for expression or translation of a targeted protein.

Once introduced into a cell, the antisense oligonucleotide hybridizes to its corresponding mRNA sequence through Watson-Crick binding, forming a heteroduplex. Once a duplex is formed, translation of the protein coded by the sequence of bound mRNA is inhibited. There are several mechanisms through which the oligonucleotide/mRNA duplex may hinder subsequent translation. The most widely accepted explanation for several different antisense agents involves the degradation of the mRNA in the heteroduplex by the ubiquitous enzyme RNase H. RNase H is attracted to the heteroduplex and cleaves the bound mRNA, while leaving the oligonucleotide sequence intact, allowing the oligonucleotide to continue seeking and binding to corresponding mRNA sequences. Some other accepted explanations of translation inhibition through antisense therapy which may occur separately or in conjunction with RNase H activity include, but are not limited to, the blocking of appropriate ribosome assembly that disables the ribosomal complexes' ability to translate, blocking of RNA splicing, and/or impeding appropriate exportation of mRNA.

An apparently separate means used by organisms to control gene expression by limiting translation is known as gene interference, which involves the deployment of short RNA sequences which "silence" the target gene. These short RNA sequences are known as small interfering RNAs or siRNAs. RNA interference is an ancient genetic process in which targeted genes, the blueprints for producing certain proteins, can be turned off.

An enzyme known as Dicer is known to play a key role in RNA interference. Dicer is a ribonuclease that recognizes double-stranded RNA molecules and cuts them into short dsRNAs about 20-25 nucleotides long, usually with a two-base overhang on the 3' end. The small dsRNA fragments created by Dicer are then assimilated into a large multiprotein complex which guide the dsRNA molecules to destinations in the cell where they bind to their target mRNA sequence and turn off genes. This complex is known as the RNA-induced silencing complex (RISC). RISC has a catalytic component, argonaute, which is an endonuclease capable of degrading messenger RNA (mRNA) if the mRNA has a sequence complementary to that of the siRNA guide strand. Dicer, RISC and the siRNA gene silencing system is therefore a necessary step in many fundamental biological events, including genome rearrangement, stem-cell differentiation, brain development, and viral defense.

Interestingly, it has been determined that the size of the small dsRNAs—the siRNAs—is a determinant of their function. If the dsRNAs are too big or too small, they don't make it into the RISC complexes and so no gene silencing occurs.

Antisense oligomers differ from siRNAs in several ways, most importantly, antisense oligomers are single-stranded. They are also synthetic, and typically modified along the phosphate backbone, and often in select positions of the nucleobases.

In the field of antisense therapy, the introduction of chemically modified nucleosides into nucleic acid molecules, particularly into ribonucleic acid molecules (RNA), provides a powerful tool in overcoming potential limitations of in vivo stability and bioavailability inherent to native RNA or DNA molecules that are delivered exogenously. For example, the use of chemically modified nucleic acid molecules can enable a lower dose of a particular nucleic acid molecule for a given therapeutic effect since chemically modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically modified nucleic acid molecule is reduced as compared to a native nucleic acid molecule, for example when compared to an all RNA nucleic acid molecule, the overall activity of the modified nucleic acid molecule can be greater than the native molecule due to improved stability and/or delivery of the molecule.

One useful chemical modification, termed a locked nucleic acid (LNA), introduces a 2'O-4'C-alkylene bridge wherein the alkylene bridge is a $C_{1-6}$ alkylene bridge, more particularly, a 2'O-4'C-methylene bridge, at one or more RNA or DNA nucleoside moiety. When LNAs are incorporated into antisense RNA or DNA oligomers they have been shown to greatly increase the stability of the antisense RNA or DNA molecule, and thus to greatly increase bioavailability of the antisense RNA or DNA once it is taken up by the host cell. Other useful chemical modifications that can be introduced into the antisense RNA or DNA oligomers to increase stability and bioavailability of the antisense oligomer include phosphorothioate bonds, or phosphotriester bonds, substituted in place of naturally occurring phosphodiester bonds between the individual RNA or DNA nucleotides.

SUMMARY OF THE INVENTION

In a first embodiment of the invention there is provided a pharmaceutical composition comprising an RNA or DNA oligomer according to the invention, the RNA or DNA oligomer, or a pharmaceutically acceptable salt, hydrate, solvate or ester thereof, essentially complementary to the RNA transcripts corresponding to the DNA sequences CCTGCTG-GTGGCTCCAGTTC (SEQ ID NO: 1); AGAGTCTA-GACTCGTGGTGGACTTCTCTCAATTTTCTAGGGG (SEQ ID NO:2); TGGATGTGTCTGCGGCGTTTTATCAT (SEQ ID NO: 3); CATCCTGCTGCTATGCCTCATCT-TCTT (SEQ ID NO: 4); CAAGGTATGTTGCCCGT (SEQ ID NO: 5); TGTATTCCCATCCCATC (SEQ ID NO: 6); CCTATGGGAGTGGGCCTCAG (SEQ ID NO: 7); TGGCT-CAGTTTACTAGTGC (SEQ ID NO: 8); GGGCTTTC-CCCCACTGT (SEQ ID NO: 9); TCCTCTGCCGATCCAT-ACTGCGGAACTCCT (SEQ ID NO: 10); CGCACCTCTCTTTACGCGG (SEQ ID NO: 11); GGAGT-GTGGATTCGCAC (SEQ ID NO: 12); or GAAGAA-GAACTCCCTCGCCT (SEQ ID NO: 13), incorporated by reference herein, wherein the antisense RNA or DNA molecule comprises a plurality of modified nucleosides and/or nucleotides; and a pharmaceutically acceptable diluent.

In a second embodiment of the invention there is provided a pharmaceutical composition comprising an RNA or DNA oligomer according to the invention, the RNA or DNA oligomer, or a pharmaceutically acceptable salt, hydrate, solvate or ester thereof, essentially complementary to the RNA transcripts corresponding to the DNA sequences GAGAGAAGTCCACCAC (SEQ ID NO: 14); TGAGAGAAGTCCACCA (SEQ ID NO:15); GAGGCATAGCAGCAGG (SEQ ID NO: 16); TGAGGCATAGCAGCAG (SEQ ID NO: 17); GATGAGGCATAGCAGC (SEQ ID NO: 18); GATGGGATGGGAATAC (SEQ ID NO: 19); GGCCCACTCCCATAGG (SEQ ID NO: 20); AGGCCACTCCCATAG (SEQ ID NO: 21); or CTGAGGCCACTCCCA (SEQ ID NO: 22, incorporated by reference herein, wherein the antisense RNA or DNA molecule comprises a plurality of modified nucleosides and/or nucleotides; and a pharmaceutically acceptable diluent.

One embodiment provides an antisense oligomer for use in reducing the amount of a hepatitis B virus DNA and HBV antigen in a mammalian cell or an organism, wherein the antisense oligomer is a contiguous sequence of from 10 through 26 nucleosides in length and has a sequence as set forth in formula 1:

$$5'\text{-LNA}_n\text{-P-LNA}_p\text{-P-N}_m\text{-P-N}_r\text{P-LNA}_l\text{P-LNA}_q\text{-3'} \quad \text{(formula 1)}$$

wherein LNA is a locked nucleic acid; P is an internucleoside linkage selected from a phosphodiester, phosphotriester, phosphorothioate, phosphorodithioate, H-phosphonate, or alkylphosphonate linkage between a LNA and a contiguous N, or between a N and a contiguous N, or between N and a contiguous LNA, or between a LNA and a contiguous LNA, from a 5'- to 3' direction of the sequence of formula (I); and wherein N is selected from a G, C, A, T, U, or Z nucleoside unit; n and r and p and q are each independently an integer selected from 1, 2 or 3; l and m are each independently an integer from 1 through 22; and wherein Z is selected from an inosine, $N^7$-methylinosine, $N^7$-methyl guanidine, 5-methyl uridine, 5-methyl-cytidine, 5-fluorouridine, 5-fluorothymidine, xanthosine, dihydrouridine, pseudouridine, 2-aminoadenosine, 2-thiothymidine, 7-methyl-7-deazaguanosine, 7-ethyl-7-deazaguanosine, N4-methylcytidine, N4-ethylcytidine; or a salt, solvate, hydrate or ester thereof.

Particular embodiments provide an antisense oligomer as described, wherein at least 4 of the nucleoside units of the oligomer may be LNA units. In some embodiments, the LNA is a locked nucleic acid unit having a 2'-O-alkyl-4'C linkage wherein the alkyl may be a substituted or unsubstituted $C_{1-6}$ alkyl. In additional embodiments, at least two of the internucleoside linkages present between the nucleoside units of the contiguous nucleoside sequence are phosphorothioate internucleoside linkages. In some related embodiments, all the internucleoside linkages present between the nucleoside units of the contiguous nucleoside sequence of the antisense oligomer may by phosphorothioate internucleoside linkages.

In some particular embodiments, n, p, r and q are each independently 1 or 2, and l and m are each independently 2, 3, 4, 5 or 6, and in some particular embodiments, n, p, r and q are each independently 1, and l and m are each independently 6. In other particular embodiments, there is provided an antisense oligonucleotide wherein the sequence may be any one of SEQ ID NOs 14, 16, 16 or 20.

In particular embodiments, the antisense oligomers described above may be essentially complementary to any one of SEQ ID NOs. 1-13, and the hepatitis B virus may be a human hepatitis B virus and the cell or organism may be human. In related particular embodiments, the hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

In particular embodiments, the antisense oligomers described above may have a sequence that is essentially any one of SEQ ID NOs. 14-22, and the hepatitis B virus may be a human hepatitis B virus and the cell or organism may be human. In related particular embodiments, the hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

A particular embodiment provides a pharmaceutical formulation for treating hepatitis B virus infection in a mammal comprising an effective amount of any nucleic acid antisense oligomer as described above, or a pharmaceutically acceptable salt, solvate, hydrate or ester thereof, and a pharmaceutically acceptable diluent. The antisense oligomer of such pharmaceutical formulation may be essentially complementary to any one of SEQ: ID NOs 1-13, or may have a sequence that is essentially any one of SEQ ID NOs 14-22, and may further comprise a pharmaceutically acceptable carrier.

Another embodiment of the invention provides a method for treating a hepatitis B virus infection or a hepatitis B virus-related condition in a mammal, the method comprising administering a therapeutically effective amount of any pharmaceutical composition as described above to a mammal in need thereof, so as to treat the hepatitis B virus infection, or the hepatitis B virus-related condition. In related embodiments, the mammal is a human and the hepatitis B virus infection or the hepatitis B virus-related condition is a hepatitis B virus infection from a human hepatitis B virus. More particularly, the human hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

Related embodiments provide a method for treating a hepatitis B virus infection or a hepatitis B virus-related condition in a mammal, the method comprising administering a therapeutically effective amount of any pharmaceutical composition as described above to a mammal in need thereof, as described above, wherein the human hepatitis B virus-related condition may be jaundice, liver cancer, liver inflammation, liver fibrosis, liver cirrhosis, liver failure, diffuse hepatocellular inflammatory disease, hemophagocytic syndrome or serum hepatitis.

In related embodiments, the method may further comprise administering the antisense oligomer in combination with an additional therapeutic agent, wherein the antisense oligomer and the additional therapeutic agent are administered either together in a single formulation, or administered separately in different formulations, and wherein the administration of the nucleic acid oligomer and the second therapeutic agent is done concomitantly, or in series.

In other related embodiments, the additional therapeutic agent may be an HBV agent, an HCV agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent.

In particular related embodiments, the additional HBV agent may be interferon alpha-2b, interferon alpha-2a, and interferon alphacon-1 (pegylated and unpegylated), ribavirin;

an HBV RNA replication inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In other particular related embodiments, the additional HCV agent may be interferon alpha-2b, interferon alpha-2a, and interferon alphacon-1 (pegylated and unpegylated); ribavirin; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

Another embodiment provides a method for reducing an amount of HBV DNA and an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV DNA and the amount of HBV antigen in the mammal before treatment. In some embodiments, the mammal may be human, and the hepatitis B virus may be a human hepatitis B virus. More particularly, the human hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

In particular embodiments, a method is provided for reducing an amount of HBV DNA and an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV DNA and the amount of HBV antigen in the mammal before treatment, wherein the amount of DNA is reduced 90% compared to the amount before administration of the antisense oligomer. In related methods, the HBV antigen may be HBsAg or may be HBeAg, and more particularly, the amount of HBV antigen may be sufficiently reduced to result in seroconversion, defined as serum HBeAg absence plus serum HBeAb presence if monitoring HBeAg as the determinant for seroconversion, or defined as serum HBsAg absence if monitoring HBsAg as the determinant for seroconversion, as determined by currently available detection limits of commercial ELISA systems.

In more particular embodiment, a method as described above may further comprise administering the antisense oligomer in combination with an additional therapeutic agent, wherein the antisense oligomer and the additional therapeutic agent are administered either together in a single formulation, or administered separately in different formulations, and wherein the administration of the nucleic acid oligomer and the second therapeutic agent is done concomitantly, or in series. In particular related embodiments, the additional therapeutic agent may be an HBV agent, an HCV agent, a chemotherapeutic agent, an antibiotic, an analgesic, a non-steroidal anti-inflammatory (NSAID) agent, an antifungal agent, an antiparasitic agent, an anti-nausea agent, an antidiarrheal agent, and an immunosuppressant agent. In more particular related embodiments, the additional HBV agent may be interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir; tenofovir; telbivudine (LdT); adefovir; or an HBV antibody therapy (monoclonal or polyclonal), and the additional HCV agent may be interferon alpha-2b, interferon alpha-2a, and interferon alphacon-1 (pegylated and unpegylated); ribavirin; an HCV RNA replication inhibitor (e.g., ViroPharma's VP50406 series); an HCV antisense agent; an HCV therapeutic vaccine; an HCV protease inhibitor; an HCV helicase inhibitor; or an HCV antibody therapy (monoclonal or polyclonal).

Another embodiment provides a method for promoting seroconversion of a hepatitis B virus in a mammal infected with HBV, the method comprising administering a therapeutically effective amount of a pharmaceutical composition as described above to a mammal infected with hepatitis B; monitoring for presence of HBeAg plus HBeAb in a serum sample of the mammal, or monitoring for presence of HBsAg in a serum sample of the mammal, such that the absence of HBeAg plus the presence of HBeAb in the serum sample if monitoring HBeAg as the determinant for seroconversion, or the absence of HBsAg in the serum sample if monitoring HBsAg as the determinant for seroconversion, as determined by current detection limits of commercial ELISA systems, is indication of seroconversion in the mammal.

For any of the embodiments described herein which provide a method of treating a hepatitis B virus infection or hepatitis B virus-related condition, a method for reducing an amount of HBV DNA and an amount of HBV antigen in a mammal infected with a hepatitis B virus, or a method for promoting seroconversion of a hepatitis B virus in a mammal infected with HBV, wherein the method comprises administration of an antisense oligomer as described herein, administration of the antisense oligomer, whether alone or in combination, and whether present in a pharmaceutical formulation or simply present in a diluent, the administration may be oral, buccal, rectal, parenteral, intraperitoneal, intradermal, transdermal or intratracheal administration.

BRIEF DESCRIPTION OF THE DRAWINGS

The foregoing features of the invention will be more readily understood by reference to the following detailed description, taken with reference to the accompanying drawings, in which:

FIG. 6 is a table of various HBV geographical genotypes that have been identified.

DETAILED DESCRIPTION OF SPECIFIC EMBODIMENTS

Figure 1:
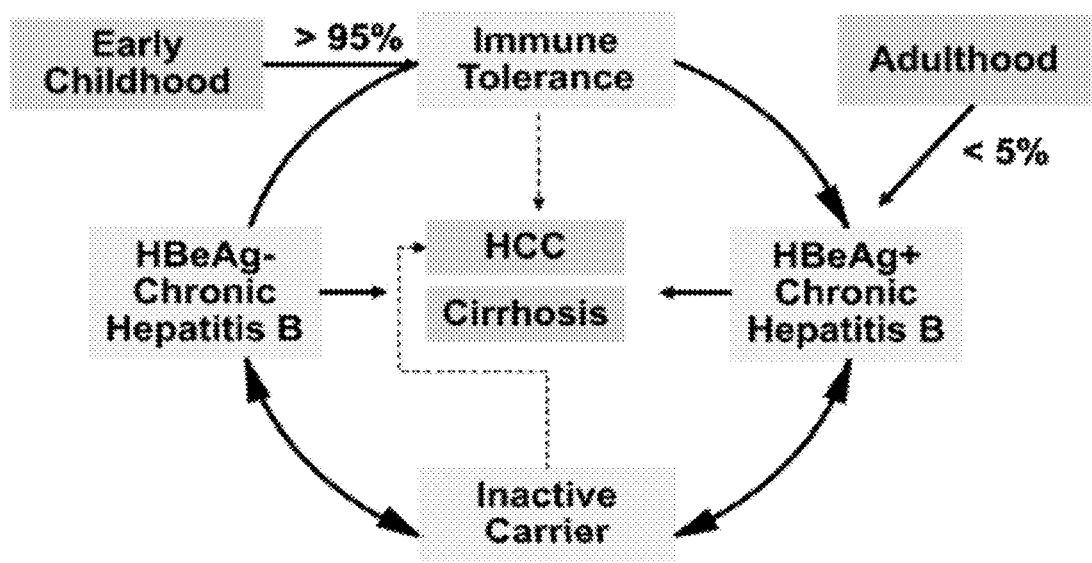
FIG. 1 is a diagram of the natural history of HBV infection.

Definitions. As used in this description and the accompanying claims, the following terms shall have the meanings indicated, unless the context otherwise requires:

As used herein, the term "effective amount" means that amount of a drug or drug substance, or pharmaceutical agent, including a nucleic acid oligomer, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "essentially complementary" means that the antisense oligomer sequence has a sequence completely complementary to its target sense sequence using the standard Watson-Crick base pairs A-T, A-U and G-C. In addition, the term essentially complementary includes an antisense oligomer sequence completely complementary to its target sense sequence, using non-standard Watson-Crick base pairs including, but not limited to, G:U, I:U, I:A, I:C, X:A, X:C, R:C, R:T, R:U, m7I:U, m7I-A, m7I:C, m7G:U, m7G:C, m5U:A, 5-FU:A, 5-FT:A, m5C:G, D:A, LP:A, and 4):C. As used herein, G is guanosine, I is inosine, A is adenosine, C is cytidine, U is uridine, T is thymidine, X is xanthosine, R is ribavirin, m7G is N7-methylguanosine, m7I is N7-methylinosine, 5FU is 5-fluorouridine, 5FT is 5-fluorothymidine, D is dihydrouridine, m5U is 5-methyluridine, m5C is 5-methylcytidine, and ψ is pseudouridine.

The term "essentially complementary" also encompasses antisense oligomers that have one or more synthetic nucleobases in the sequence that exhibit pseudo-complementarity to naturally occurring nucleobases in a DNA or RNA target nucleic acid sequence. Examples of nucleobases that result in pseudo-complementarity with natural nucleic acid sequences include 2-aminoadenine or 2-aminoadenosine (nA), 2-thiothymine or 2-thiothymidine (sT), 7-alkyl-7-deazaguanine or 7-alkyl-7 deazaguanosine (7a1-7daG) and N4-alkylcytosine or N4-alkylcytidine (N-4-aIC; where alkyl=methyl or ethyl). The non-Watson-Crick base pairs nA:T and A:sT are stable base pairs, as are 7-alkyl-7-deazaguanine with C (7a1-7daG: C) and N4-alkylcytosine with G (N-4-aIC:G). When all four synthetic nucleobases nA, sT, 7a1-7daG and N4-aIC are incorporated into a given ASO, the resulting ASO sequence will be largely free of secondary structure and will bind to a target nucleic acid with pseudo-complementary. In embodiments of the present invention, one or more synthetic nucleobases may be present in the ASO sequence, resulting in one or more non-Watson-Crick "pseudo-complementary" bases pairs between the ASO and the target nucleic acid sequence. It is understood that an ASO having one or more pseudo-complementary bases, thereby forming one or more pseudo base pairs with nucleobases on the target nucleic acid sequence, will be considered to be essentially complementary to the target nucleic acid sequence.

The term "essentially", such as when used with the phrase "an oligonucleoside that has essentially the sequence of SEQ ID NO X" is used herein to mean any sequence that could base-pair with a complementary sequence to SEQ ID NO X, as written, but which may contain one or more synthetic nucleobases in the sequence that exhibit pseudo-complementarity to naturally occurring nucleobases in a DNA or RNA target nucleic acid sequence. Examples of nucleobases that result in pseudo-complementarity with natural nucleic acid sequences include 2-aminoadenine or 2-aminoadenosine (nA), 2-thiothymine or 2-thiothymidine (sT), 7-alkyl-7-deazaguanine or 7-alkyl-7 deazaguanosine (7aI-7daG) and N4-alkylcytosine or N4-alkylcytidine (N-4-aIC; where alkyl=methyl or ethyl). The non-Watson-Crick base pairs nA:T and A:sT are stable base pairs, as are 7-alkyl-7-deazaguanine with C (7aI-7daG:C) and N4-alkylcytosine with G (N-4-aIC:G). When all four synthetic nucleobases nA, sT, 7aI-7daG and N4-aIC are incorporated into a given ASO, the resulting ASO sequence will be largely free of secondary structure and will bind to a target nucleic acid with pseudo-complementary. In embodiments of the present invention, one or more synthetic nucleobases may be present in the ASO sequence, resulting in one or more non-Watson-Crick "pseudo-complementary" bases pairs between the ASO and the target nucleic acid sequence. It is understood that an ASO having one or more pseudo-complementary bases, thereby forming one or more pseudo base pairs with nucleobases on the target nucleic acid sequence, will be considered to have essentially the sequence of SEQ ID NO X, as written, directed to a given target nucleic acid sequence.

The term "nucleic acid oligomer" as used herein means a nucleic acid molecule comprising at least 2 and no more than 100 consecutively-linked covalently bonded nucleoside or nucleotide units. Each individual nucleoside or nucleotide unit may comprise a ribose or a deoxyribose sugar, and thus the oligomer may comprise a combination of ribose and deoxyribose sugars. The nucleotides or nucleosides in the nucleic acid oligomer may be linked so the oligomer comprises traditional phosphodiester linkages, or alternatively the oligomer may comprise one or more phosphotriester linkage, phosphonate linkage, alkylphosphonate linkage, phosphorothioate linkage, or phosphorodithioate linkage. In addition, the nucleic acid oligomer may comprise one or more modified nucleosides, including 2'O-4'C linked nucleosides, and in addition, or alternatively, the nucleic acid oligomer may comprise one or more nucleosides with other modifications at the 2'-position, including a 2'-O-alkyl modifications such as 2'-O-methyl modification, 2'-O-ethyl modification, or other 2'-modifications.

The term LNA (locked nucleic acid) as used herein encompasses nucleic acid monomers having a chemical link between the 2'- and 4'-position of the nucleoside sugar unit, (i.e. the furanose sugar of a nucleic acid monomer has a 2'O-4'C link, or 4'C-2'O link, if described according to the generally accepted naming from the 5'- to 3'-directionality of an oligonucleotide), including but not limited to A) α-L-Methyleneoxy (4'-CH$_2$—O-2') LNA, (B) 13-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

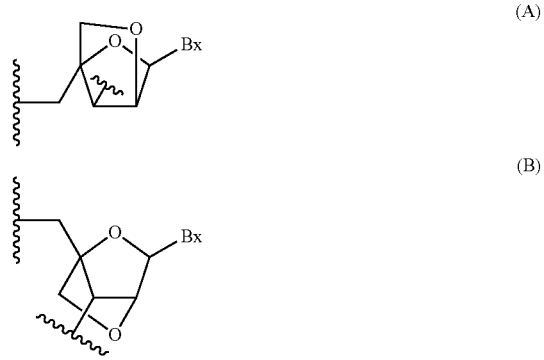

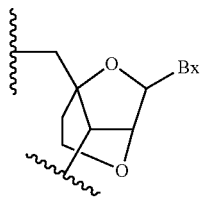
(C)

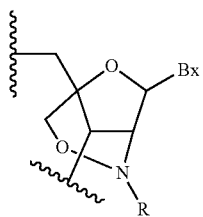
(D)

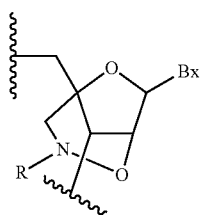
(E)

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —S(=O)— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of specific 4'C-2'O bridges encompassed within the definition of LNA include —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)— bridges. Other bridges encompassed with the definition of LNA are 4'-CH$_2$-2',4'-(CH$_2$)$_2$-2',4'-(CH$_2$)$_3$-2', 4'-CH$_2$—O-2',4'-(CH$_2$)$_2$—O-2',4'-CH$_2$—O—N(R$_1$)-2' and 4'-CH$_2$—N(R$_1$)—O-2'-bridges, wherein each R$_1$ is, independently, H, a protecting group or C$_1$-C$_{12}$ alkyl.

Also included within the definition of LNA according to the invention are LNAs in which the 2'-hydroxyl group of the ribosyl sugar ring is linked to the 4' carbon atom of the sugar ring thereby forming a methyleneoxy (4'-CH$_2$—O-2') linkage to form the bicyclic sugar moiety. The linkage can be a methylene (—CH$_2$—) group bridging the 2' oxygen atom and the 4' carbon atom, for which the term methyleneoxy (4'-CH$_2$—O-2') LNA is used for the bicyclic moiety; in the case of an ethylene group in this position, the term ethyleneoxy (4'-CH$_2$CH$_2$—O-2') LNA is used. Alpha-L-methyleneoxy (4'-CH$_2$—O-2'), an isomer of methyleneoxy (4'-CH$_2$—O-2') LNA is also encompassed within the meaning of LNA, as used herein.

The term "2'-O-alkyl-4'C linkage" as used herein refers to a 2'-O-4'-C (or 4'C-2'O, if described according to the generally accepted naming from the 5'- to 3'-directionality of an oligonucleotide) chemical linkage, or bridge, in a locked nucleic acid (LNA). The alkyl linkage may be a substituted or non-substituted alkyl, wherein "alkyl", as used herein, means —[C(R$_1$)(R$_2$)]$_n$—, wherein n is 1, 2, 3, 4, 5 or 6; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, OJ$_1$, NJ$_1$J$_2$, SJ$_1$, N$_3$, OOOJ$_1$, acyl (C(=O)—H), and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_1$-C$_{12}$ aminoalkyl, substituted C$_1$-C$_{12}$ aminoalkyl or a protecting group.

As used herein, the term "HBV" means mammalian hepatitis B virus, including human hepatitis B virus. The term encompasses geographical genotypes of hepatitis B virus, particularly human hepatitis B virus, as well as variant strains of geographical genotypes of hepatitis B virus.

As used herein, "hepatitis B-related condition" or "HBV-related condition" means any disease, biological condition, medical condition, or event which is exacerbated, caused by, related to, associated with, or traceable to a hepatitis B infection, exposure, or illness. The term hepatitis B-related condition includes jaundice, liver cancer, liver inflammation, liver fibrosis, liver cirrhosis, liver failure, diffuse hepatocellular inflammatory disease, hemophagocytic syndrome, serum hepatitis, HBV viremia, and conditions having symptoms which may include any or all of the following: flu-like illness, weakness, aches, headache, fever, loss of appetite, diarrhea, jaundice, nausea and vomiting, pain over the liver area of the body, clay- or grey-colored stool, itching all over, and dark-colored urine, when coupled with a positive test for presence of a hepatitis B virus, a hepatitis B viral antigen, or a positive test for the presence of an antibody specific for a hepatitis B viral antigen.

The antisense oligonucleotides (ASOs) of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. D$_2$O, d$_6$-acetone, d$_6$-DMSO.

Included within the scope of the claimed compounds present invention are all stereoisomers, geometric isomers and tautomeric forms of the compounds of formula (I), including compounds exhibiting more than one type of isomerism, and mixtures of one or more thereof.

The ASOs of the present invention may be administered as prodrugs. Thus, certain derivatives of the ASOs described herein, which may have little or no pharmacological activity themselves can, when administered into or onto the body, be converted into ASOs essentially complementary to SEQ ID NOs: 1-13 having the desired activity, for example, by hydrolytic cleavage. Such derivatives are referred to as 'prodrugs'.

Depending on the nature of the specific antisense nucleic acid oligomer, the ASO may be administered to the host using any convenient means capable of resulting in the desired reduction of target viral transcripts, viral genome amount or load in the target cell. Thus, the antisense oligomer can be incorporated into a variety of formulations for therapeutic administration. More particularly, the antisense oligomers of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the antisense oligomers can be achieved in various ways, including oral, buccal, rectal, parenteral, intraperitoneal, intradermal, transdermal, intratracheal, etc., administration.

In pharmaceutical dosage forms, the ASOs may be administered alone or in appropriate association, as well as in combination, with other pharmaceutically active agents. The following methods and excipients are merely exemplary and are in no way limiting. The ASOs described herein can be administered in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like).

For oral preparations, the ASOs can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The ASOs can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Liquid pharmaceutically administrable compositions can, for example, be prepared by dissolving, dispersing, etc. at least one ASO and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of ASO contained in such parenteral compositions is highly dependent on the specific nature thereof, as well as the activity of the ASO and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent ASO in solution.

The ASO agents can be utilized in aerosol formulation to be administered via inhalation. The ASOs of the present invention can be formulated into pressurized acceptable propellants such as dichlorodifluoromethane, propane, nitrogen and the like. For delivery via inhalation the ASO can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Furthermore, the ASO agents can be made into suppositories by mixing with a variety of bases such as emulsifying bases or water-soluble bases. The ASOs of the present invention can be administered rectally via a suppository. The suppository can include vehicles such as cocoa butter, carbowaxes and polyethylene glycols, which melt at body temperature, yet are solidified at room temperature.

In general, the ASO agents provided will be administered in a therapeutically effective amount by any of the accepted modes of administration for ASO agents that serve similar utilities. The actual amount of the antisense oligomer, i.e., the active ingredient, will depend upon numerous factors such as the severity of the disease to be treated, the age and relative health of the subject, the potency of the ASO used, the route and form of administration, and other factors. The pharmaceutical composition can be administered more than once a day, such as once or twice a day. In particular embodiments, the ASO pharmaceutical formulation will be administered once or twice per week over the course of 24, 36, or 48 weeks or longer, as needed, to effectively treat the HBV infection, including to reduce viral load, to reduce viral antigens, produce seroconversion, bolster the subjects immune response and/or decrease HBV DNA levels and normalize alanine transferase (ALT) levels.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific ASO agent, the nature of the delivery vehicle, and the like. Preferred dosages for a given ASO are readily determinable by those of skill in the art by a variety of means.

Examples of delivery methods for administration of the ASO therapeutic agents described herein, as well as details of pharmaceutical formulations, solvates, hydrates, salts and esters are well-known to one of skill in the art and are described in the literature.

An effective amount of an ASO inhibitory agent may be introduced into the target cell using any convenient protocol for introducing an ASO agent into a target cell. Methods include use of agents such as lipofectamine, polycationic amines, such as spermine, spermidine and the like, as well as methods involving electroporation, microinjection, liposome encapsulation, and more, according to standard protocols available in the art. In some cases no exogenous agent is necessary for uptake of the ASO into the target cell. Introduction of an effective amount of an ASO agent into a mammalian cell results in a modulation, i.e. reduction, of HBV target gene(s) expression, leading to reduction in HBV load, reduced HBV DNA, normalized ALT activity, seroconversion, cure, and improved immune response.

Ultimately, the choice of formulation and dosage depends on various factors such as the mode of drug administration and bioavailability of the drug substance.

The methods of the present invention will work in any mammalian cell, where representative mammal cells of interest include, but are not limited to cells of: ungulates or hooved animals, e.g., cattle, goats, pigs, sheep, etc.; rodents, e.g., hamsters, mice, rats, etc.; lagomorphs, e.g., rabbits; primates, e.g., monkeys, baboons, humans, etc.; and the like.

The ASO compositions may be advantageously combined and/or used in combination and/or alternation with other antiviral agents which are either therapeutic or prophylactic agents, and different from the subject compounds. The compositions may also be advantageously combined and/or used in combination with agents that treat conditions often associated with the viral infections that are sensitive to the present compounds, such as anti-HCV agents or immunosuppressive agents. In certain embodiments, administration in conjunction with the subject compositions enhances the efficacy of such agents. Accordingly, the present compounds, when combined or administered in combination with other antiviral agents, can be used in certain embodiments in dosages which are less than the expected amounts when used alone, or less than the calculated amounts for combination therapy.

The ASOs and ASO compositions of the present invention may also be used with agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

As will be understood by those skilled in the art, dosing depends on the severity and responsiveness of the disease state to be treated, and the course of treatment lasting from several days to several months, or until a cure is effected or a diminution of the disease state is achieved. Optimal dosing schedules can be calculated from measurement of ASO active agent accumulation in the body of the patient. Optimum dosages may vary depending on the relative potency of individual oligonucleotides. Generally it can be estimated based on EC50s found to be effective in vitro and in in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state. More particularly, the course of treatment will last for approximately 48 weeks, administered once per week, as a subcutaneous injection at doses from about 0.01 µg/kg body weight to about 1 g/kg body weight.

Embodiments of the invention relate to a pharmaceutical composition, which comprises at least one antisense oligomer of the invention as an active ingredient. It should be understood that the pharmaceutical composition according to the invention includes a diluent, and optionally comprises a pharmaceutical carrier, and that the pharmaceutical composition optionally comprises further compounds, such as chemotherapeutic compounds, anti-inflammatory compounds, antiviral compounds, analgesics, NSAIDs, narcotics, antibiotics, antifungal compounds, antiparasitic compounds, and/or immuno-modulating compounds.

The oligonucleotides of the invention can be used "as is" or in form of a variety of pharmaceutically acceptable salts. As used herein, the term "pharmaceutically acceptable salts" refers to salts that retain the desired biological activity of the herein-identified oligonucleotides and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine.

In a particular embodiment of the invention, the oligonucleotide may be in the form of a pro-drug. Oligonucleotides, which in their natural form normally have the individual nucleotides linked by a phosphodiester backbone, generally exist with mostly deprotonated phosphate oxygen at pH 7, and so are negatively charged molecules. Because cell membranes are lipophilic in nature, cellular uptake of oligonucleotides is often reduced compared to neutral or lipophilic equivalents. One solution is to use the pro-drug approach (see e.g. Crooke, R. M. (1998) in Crooke, S. T. Antisense research and Application. Springer-Verlag, Berlin, Germany, vol. 131, pp. 103-140).

Pharmaceutically acceptable binding agents and adjuvants may also comprise part of the formulated drug.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of ASO composition to tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass, C R. *J Pharm Pharmacol* 2002; 54(1):3-27). The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention may be formulated into any of many possible dosage forms such as, but not limited to, tablets, capsules, gel capsules, liquid syrups, soft gels and suppositories.

The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The compounds of the invention may also be conjugated to active drug substances, for example, aspirin, ibuprofen, a sulfa drug, an antidiabetic, an antibacterial or an antibiotic, and an anticancer drug substance. In addition, the ASO sequences of the invention may be administered as a combination therapy together with, or separately in conjunction with, drug substances useful for treating cancer, inflammation, pain, bacterial, fungal and/or parasitic infections, alcoholism, substance abuse, diabetes, as well as with drug substances useful for treating other viral infections such as HIV, HCV and the like.

There are two general types of hepatitis B viral infections: acute, and chronic. Subjects who have experienced a HBV infection may also recover and become non-symptomatic carriers. Acute hepatitis B results when a person exposed to the hepatitis B virus begins to develop the signs and symptoms of viral hepatitis. This period of time, called the incubation period, is an average of 90 days, but could be as short as 45 days or as long as 6 months. For most people this infection will cause mild to moderate discomfort but will go away by itself because of the body's immune response succeeds in fighting the virus. However, some people, particularly those with compromised immune systems, such as persons suffering from AIDS, undergoing chemotherapy, taking immunosuppressant drugs, or taking steroids, have very serious problems as a result of the acute HBV infection, and go on to more severe conditions such as fulminant liver failure.

Chronic hepatitis B occurs when a person initially suffers from an acute infection but is then unable to fight off the infection. Whether the disease becomes chronic or completely resolves depends mostly on the age of the infected person. About 90% of infants infected at birth will progress to chronic disease. However, as a person ages, the risk of chronic infection decreases such that between 20%-50% of children and less than 10% of older children or adults will progress from acute to chronic infection. Chronic HBV infections are the primary treatment goal for embodiments of the present invention, although ASO compositions of the present invention are also capable of treating HBV-related conditions, such as inflammation, fibrosis, cirrhosis, liver cancer, serum hepatitis, and more.

As indicated in FIG. 1, a summary of the natural history of HBV infection, if a patient contracts HBV as during early childhood, there is a 95% chance that the child will develop immune tolerance and the condition will progress to chronic hepatitis; whereas if the patient contracts HBV as an adult, there is only a 5% chance that the condition will become chronic.

There are four phases of chronic HBV infection. The first phase is the immune tolerant phase, where minimal fibrosis and inflammation of the liver is exhibited, coupled with high HBV DNA and normal alanine aminotransferase (ALT) levels. The second phase is an immune clearance phase, where active inflammation of the liver is observable upon histology, which may also include fluctuating levels of ALT activity and fluctuating levels of HBV DNA. A third inactive carrier state phase may follow, in which infected subjects may exhibit mild hepatitis and minimal fibrosis upon histology. A fourth is also reported, termed reactivation of HBV. This last phase is characterized by active inflammation of the liver, as observed by biopsy, despite hepatitis B e antigen (HBeAg) negativity and anti-HBeAg positivity.

Chronic HBV disease is of several types. The first, known as HBeAg positive, or "wild type" HBV infection, is characterized as anti-HBeAg negative and exhibiting quantities of HBV DNA>20,000 IU/mL (>$10^5$ copies/mL). A second, known as HBeAg negative, or "mutant core" HBV infection, is characterized as anti-HBeAg positive and exhibiting HBV DNA>2,000 IU/mL (>$10^4$ copies/mL). These two types of chronic HBV infection, and historically recommended therapeutic approaches, are shown in FIGS. 2 and 3.

Figure 2:
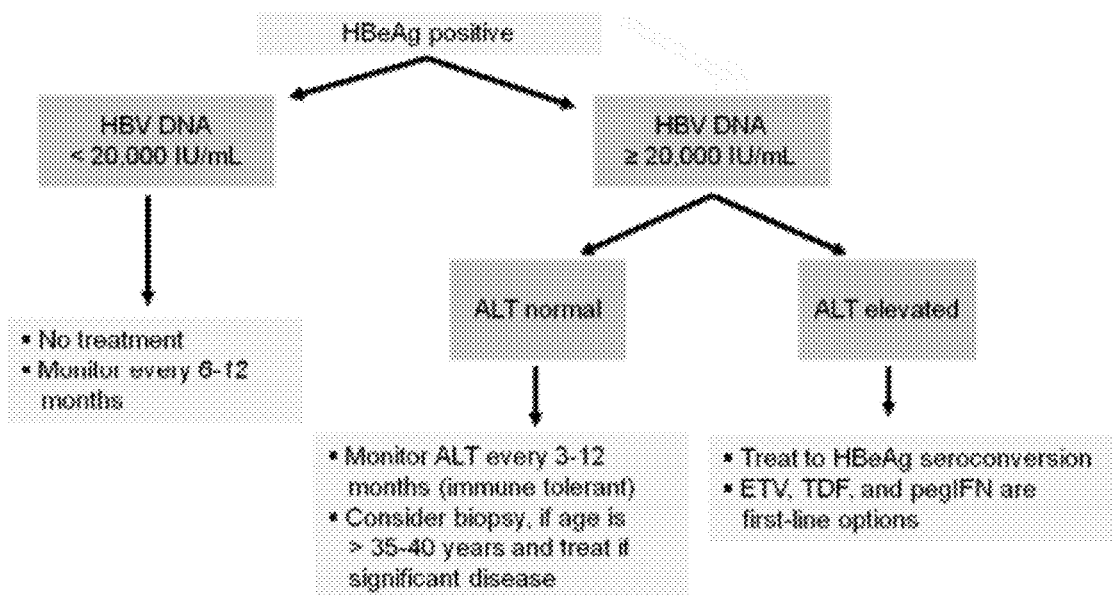
FIG. 2 is a diagram for HBV Patients with Compensated Disease who are considered HBeAg Positive.

FIG. 2 shows the categories of patients exhibiting HBeAg positive, or "wild type" HBV infection, and historical recommended treatments. On the left are those having HBV viral DNA levels less than 20,000 IU/mL (<$10^5$ copies per mL), where no treatment is recommended, other than monitoring to ensure HBV DNA levels do not increase. On the right are those having HBV viral DNA levels 20,000 IU/mL. For these patients, those with normal alanine transferase (ALT) activity are monitored every 3-12 months for any change in ALT activity, and considered for biopsy, depending on age. Those exhibiting elevated ALT activity are treated to seroconversion, although in reality, less than 20-30% of patients achieve seroconversion with current HBV therapy. The currently recommended HBV therapy includes entecavir (ETV) and tenofovir disoproxil fumarate (TDF) and peg-interferon, as primary options.

Figure 3:
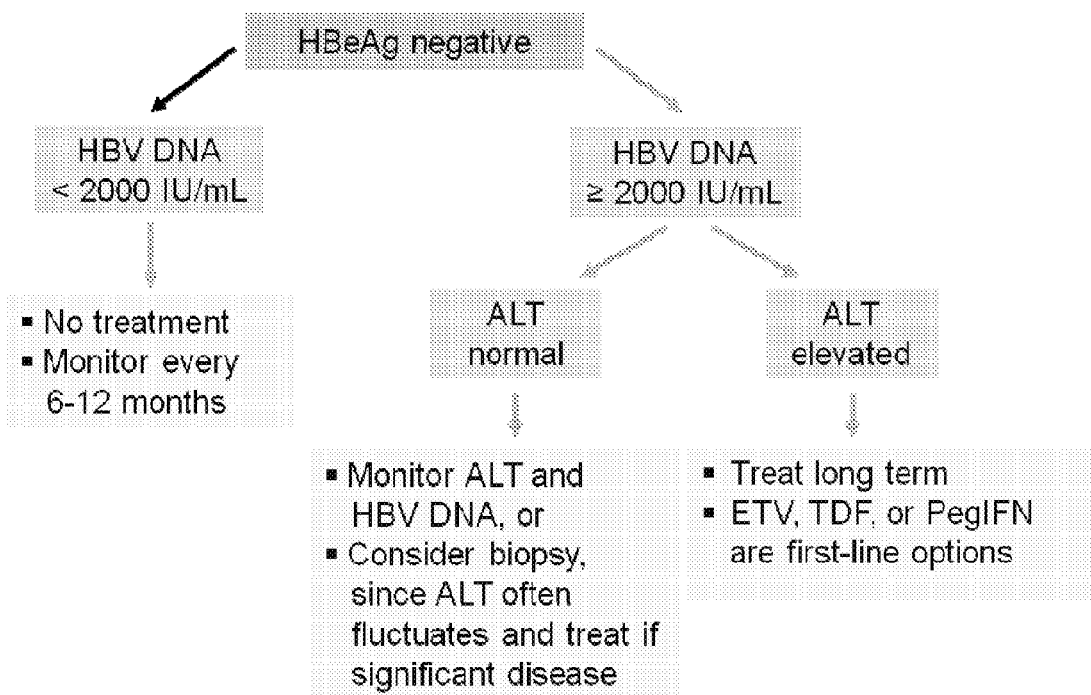
FIG. 3 is a diagram for HBV Patients with Compensated Disease who are considered HBeAg Negative.

FIG. 3 shows categories of patients exhibiting HBeAg negative, or "mutant core" HBV infection, and historical recommended treatments. On the left are those having HBV viral DNA levels less than 2,000 IU/mL (<$10^4$ copies per mL), where no treatment is recommended, other than monitoring to ensure HBV DNA levels do not increase. On the right are those having HBV viral DNA levels 2,000 IU/mL. For these patients, those with normal alanine transferase (ALT) activity are monitored for any change in ALT activity, and considered for biopsy. Those exhibiting elevated ALT activity are treated to HBsAg seroconversion, if possible, using currently recommended HBV therapy, including entecavir (ETV) and tenofovir disoproxil fumarate (TDF) and peg-interferon, as primary options.

Patients suffering from acute HBV infection produce a vigorous, polyclonal, and multispecific Cytotoxic T Lymphocyte (CTL) response to viral antigens, whereas chronically infected patients have a weak or undetectable CTL response. Hepatitis occurs when a weak HBV-specific immune response is activated that is sufficiently strong to destroy HBV-infected hepatocytes. Little is known regarding the mechanism responsible for T cell hyporesponsiveness or tolerance, but it is thought that it may involve the following mechanisms: negative selection (neonates); immunological ignorance; peripheral anergy or lack of co-stimulatory molecules, e.g. regulatory T cells (Tregs); exhaustion (up-regulation of PD-1). A common factor for all these suggested mechanisms is high levels of antigen persisting in the patient.

The HBV antigen HBeAg is a secreted, non-particulate form of HBV core protein. HBV antigens HBeAg and HBcAg share primary amino acid sequences, so show cross-reactivity at the T cell level. HBeAg is not required for viral assembly or replication, although studies suggest they may be required for establishment of chronic infection.

Neonatal infection with HBeAg-negative mutant often results in fulminant acute rather than chronic HBV infection (Terezawa et al (1991) Pediatr. Res. 29:5), whereas infection of young woodchucks with WHeAg-negative mutant results in a much lower rate of chronic WHV infection (Cote et al (2000) Hepatology 31:190). HBeAg may possibly function as a toleragen by inactivating core specific T cells through deletion or clonal anergy (Milich et al (1998) J. Immunol. 160:8102). There is a positive correlation between reduction of HBV viral load and antigens, and a decrease of expression, by T cells, of the inhibitory receptor programmed death-1 (PD-1; also known as PDCD1), a negative regulator of activated T cells, upon antiviral therapy and HBeAg seroconversion (Evans et al (2008) Hepatology 48:759).

HBV surface antigen, or HBsAg, is the envelope protein of infectious HBV viral particles but is also secreted as a non-infectious particle with serum levels 1000-fold higher than HBV viral particles. The serum levels of HBsAg in an infected person or animal can be as high as 1000 µg/mL (Kann and Gehrlich (1998) Topley & Wilson's Microbiology and Microbial Infections, $9^{th}$ ed. 745). In acute HBV infections, the half-life of HBsAg in the serum, or serum $t_{1/2}$, is 8.3 days (Chulanov et al (2003) J. Med. Virol. 69: 313). Internalization of HBsAg by myeloid dendritic cells inhibits up-regulation of co-stimulatory molecules (i.e. B7) and inhibits T cell stimulatory capacity (den Brouw et al (2008) Immunology 126:280), and dendritic cells from chronically infected patients also show deficits in expression of co-stimulatory molecules, secretion of IL-12, and stimulation of T cells in the presence of HBsAg (Zheng et al (2004) J. Viral Hepatitis 11:217).

HBsAg specific CD8 cells from CHB patients show altered tetramer binding. These CD8 cells are not anergic but may have TCR topology that confers partial tolerance or ignorance (Reignat et al (2002) J. Exp. Med. 195:1089). Moreover, reduction in serum HBsAg>1 log at week 24 has a high predictive value (92%) for sustained virological response (SVR—defined as nondetectable HBV DNA by PCR at 1 year after treatment) during Peg-IFNα2a therapy (Moucari et al (2009) Hepatology 49:1151).

Due to overlapping transmission routes, many people have been exposed to both hepatitis B virus (HBV) and hepatitis C virus (HCV), and a smaller proportion are chronically infected with both viruses, especially in regions such as Asia where HBV is endemic. Estimates suggest that up to 10% of people with HCV may also have HBV, while perhaps 20% of people with HBV are coinfected with HCV. However, treatment of hepatitis B or hepatitis B in HBV-HCV coinfected individuals has not been well studied.

Treatment is complicated by the fact that HCV and HBV appear to inhibit each other's replication (though not all studied have observed this interaction). Therefore, treatment that fully suppresses HBV could potentially allow HCV to re-emerge, or vice versa.

Therefore, ASO compounds of the present invention may advantageously be used for treating patients infected with both HBV and HCV. Exemplary treatment options for hepatitis C(HCV) include interferons, e.g., interferon alpha-2b, interferon alpha-2a, and interferon alphacon-1. Less frequent interferon dosing can be achieved using pegylated interferon (interferon attached to a polyethylene glycol moiety which significantly improves its pharmacokinetic profile). Combination therapy with interferon alpha-2b (pegylated and unpegylated) and ribavirin has also been shown to be efficacious for some patient populations. Other agents currently being developed include HCV RNA replication inhibitors (e.g., ViroPharma's VP50406 series), HCV antisense agents, HCV therapeutic vaccines, HCV protease inhibitors, HCV helicase inhibitors and HCV antibody therapy (monoclonal or polyclonal).

Embodiments of the present invention provide an ASO compound essentially complementary to any of SEQ: ID NOs 1-13, for treating a subject infected with HBV and HCV, wherein the ASO compound is administered in combination with an HCV agent. The HCV agent may be administered in the same drug formulation as the ASO compound, or may be administered in a separate formulation. Moreover, the HCV compound may be administered simultaneously as the ASO HBV compound, or may be administered separately, so that a dose of each of the HBV ASO compound and the HCV agent overlap, in time, within the patient's body. In related embodiments, the HCV agent may be selected from interferon alpha-2b, interferon alpha-2a, and interferon alphacon-1 (pegylated and unpegylated); ribavirin; an HCV RNA replication inhibitor (e.g., ViroPharma's VP50406 series); an HCV antisense agent; an HCV therapeutic vaccine; an HCV protease inhibitor; an HCV helicase inhibitor; and an HCV antibody therapy (monoclonal or polyclonal).

In another embodiment, an HBV ASO compound of the present invention may be administered to a patient infected with HBV, in combination with a second HBV therapeutic agent, wherein the second HBV therapeutic agent may be administered in the same drug formulation as the HBV ASO compound, or may be administered in a separate formulation. The second HBV therapeutic agent may be administered simultaneously with the ASO HBV compound, or may be administered separately, so that a dose of each of the HBV ASO compound and the HBV therapeutic agent overlap, in time, within the patient's body. In related embodiments, the HBV therapeutic agent may be selected from interferon alpha-2b, interferon alpha-2a, and interferon alphacon-1 (pegylated and unpegylated), ribavirin; an HBV RNA replication inhibitor; a second HBV antisense compound; an HBV therapeutic vaccine; an HBV prophylactic vaccine; lamivudine (3TC); entecavir; tenofovir; telbivudine (LdT); adefovir; and an HBV antibody therapy (monoclonal or polyclonal).

Figure 4:
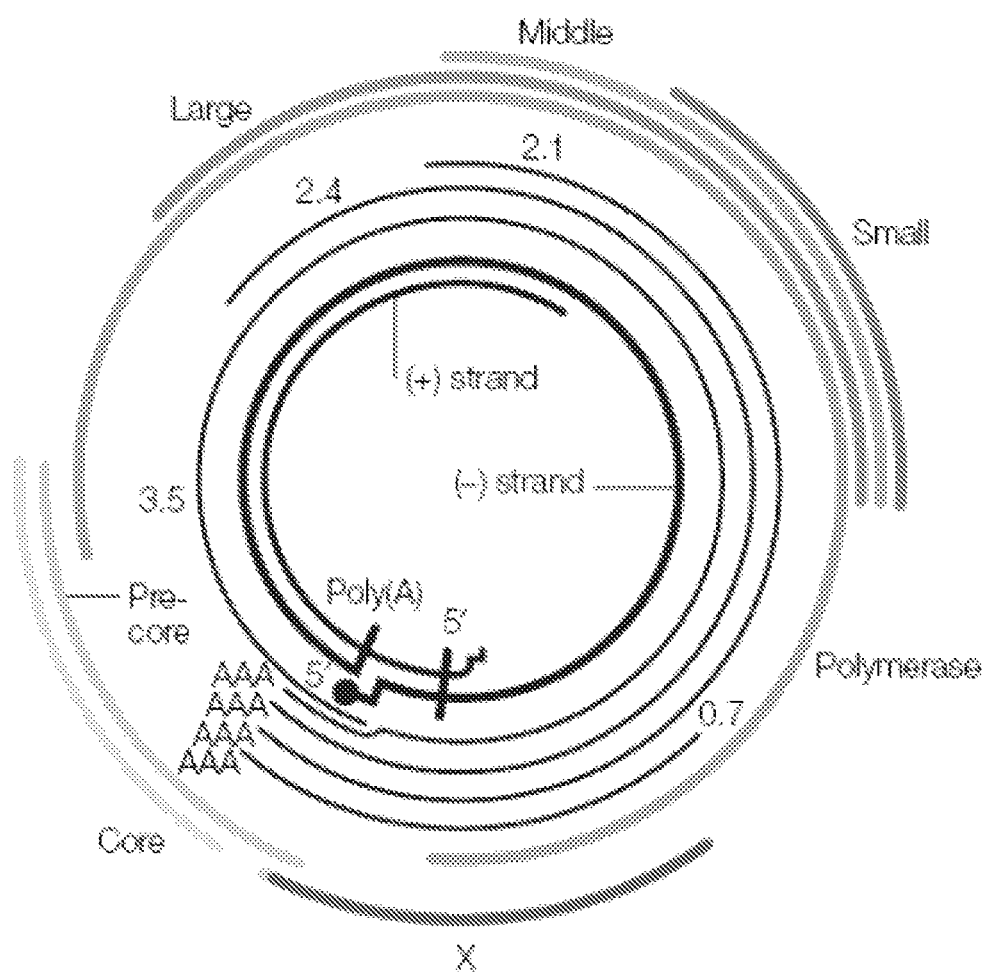
FIG. 4 is a schematic of HBV transcription, showing the major transcripts encoded by the HBV genome, including the precore and core protein, the RNA- and DNA-dependent DNA polymerase (reverse transcriptase activity), the X protein, and the large, middle and small S proteins, as well as the poly-A tails, relative lengths of the transcripts, and the overlap of the large, middle and small S protein transcripts. The plus and minus strands of the HBV DNA are also indicated.

FIG. 4 is a schematic of HBV transcription, showing the major transcripts encoded by the HBV genome, including the precore and core protein, the RNA- and DNA-dependent DNA polymerase (reverse transcriptase activity), the X protein, and the large, middle and small S proteins, as well as the poly-A tails, relative lengths of the transcripts, and the overlap of the large, middle and small S protein transcripts. The plus and minus strands of the HBV DNA are also indicated.

Figure 5:
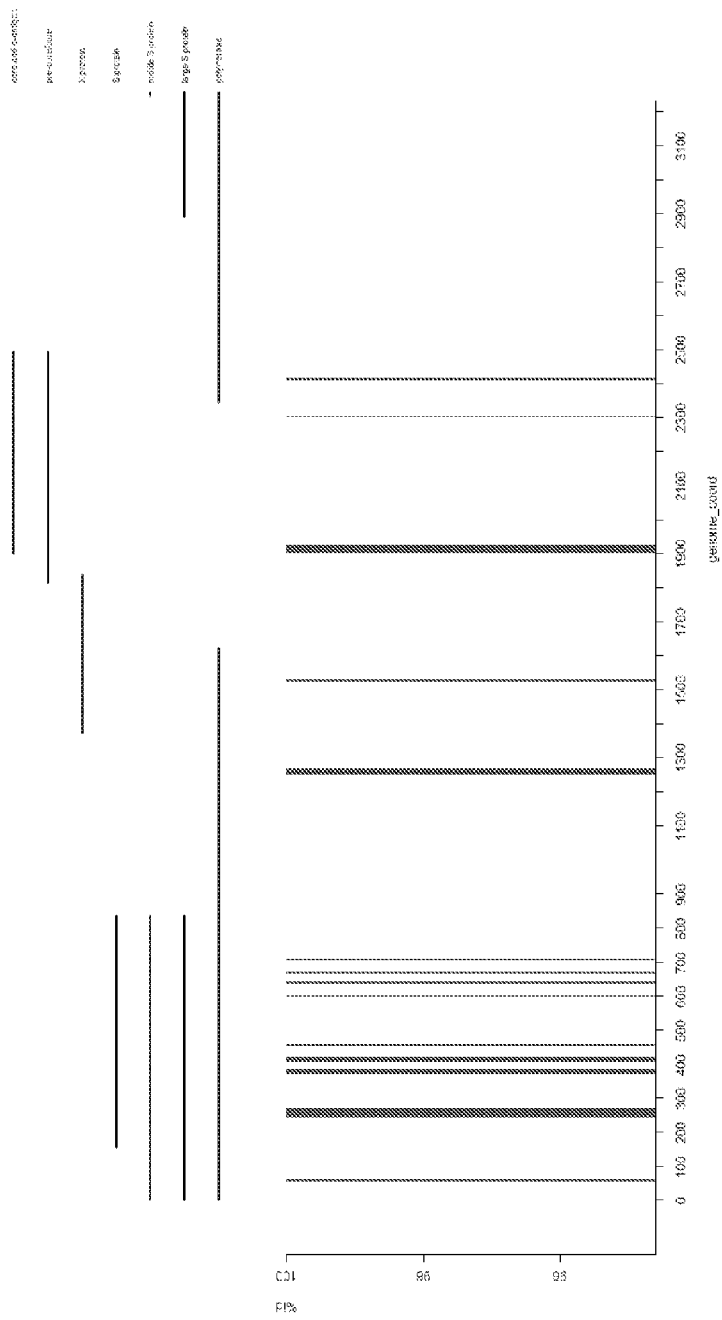
FIG. 5 shows a computational biology analysis comparing percent identity among sequences of genomic DNA from multiple genotypes of HBV, plotted by HBV genomic region.

FIG. 5 shows a computational biology analysis comparing percent identity among sequences of genomic DNA from multiple genotypes of HBV, plotted by HBV genomic region. As can be seen in FIG. 5, multiple regions of 100% identity among the sequences were identified, particularly for the polymerase and large, middle and small S protein transcribed regions.

FIG. 6 is a table of various geographical HBV genotypes. As can be seen in the table, there are eight different geographical HBV genotypes that have been categorized, which differ by approximately 8% in their genomic DNA. Besides varying in their geographical distribution, HBV genotypes may also differ in clinical history and their response to interferon therapy.

Using an expanded computation biology analysis, similar to that exemplified in FIG. 5, ~2300 sequences were analyzed and surprisingly identified 13 sequences with >95% identity across the various genotypes. This analysis has allowed the design of individual antisense oligomer sequences that each target a sequence conserved with >95% identity among multiple transcription products and regions of the HBV genome, across the genotypes. Thus, the inventors have surprisingly and unexpectedly identified a means for an individual ASO sequence to shut down multiple transcription products, and the same individual ASO will also have increased activity across all geographical HBV genotypes. Such an approach allows for a pharmaceutical composition comprising, as an active compound, a single ASO sequence, and the composition will have greatly increased efficacy over existing HBV therapies, will severely limit the ability of the HBV strain to develop resistance, and will result in a 90% or greater reduced viral load, as evidenced by the presence of HBV DNA and HBV antigens HBeAg and HBsAg. Pharmaceutical compositions of the present invention will thus offer patients suffering from chronic HBV infections an improved therapeutic treatment capable of providing complete seroconversion, and ultimately leading to a complete cure for chronic HBV infections. Such an approach will also reduce HBV-related liver conditions, such as cirrhosis, hepatocellular carcinoma (HCC), and fibrosis and inflammation, resulting in the need for fewer liver transplants and helping to prevent deaths from liver disease.

In addition, beyond a greatly improved reduction in viral load, ASOs of the present invention will provide other benefits. HBeAg is believed to have an immunosuppressive role, and HBsAg is thought to contribute to T cell exhaustion. Therefore, treatment with an ASO of the present invention will bolster a patient's immune response by reducing HBeAg and HBsAg levels, allowing the immune system to better control infection. It is also expected that reduction of HBV antigen presentation in the liver will help to minimize the extent of HBV infection flare-ups, a result of the immune system restoration, all of which will increase the chances of a complete cure of chronic HBV infection.

Methods and compositions for reducing hepatitis B viral genome amounts in a target cell are provided. In the subject methods, the expression of any of several specific HBV target proteins are inhibited in a manner sufficient to reduce the amount of viral genome in the target cell, e.g., by introducing an antisense RNA inhibitory agent in the target cell. Also provided are pharmaceutical compositions for use in practicing the subject methods. Embodiments of the subject invention finds use in a variety of applications, including the treatment of subjects suffering from a viral mediated disease condition, e.g., an HBV mediated disease condition. Such conditions include, but are not limited to, fibrosis and inflammation of the liver, cirrhosis of the liver, and hepatocellular cancer (liver cancer).

An embodiments of the present invention provide an antisense oligomer (ASOs) for treating HBV infections in mammals, including humans, wherein the ASO is essentially complementary to any one of SEQ ID NOs: 1-13 and is effective at reducing viral load or antigen levels by at least 40%, more preferably by at least 50%, still more preferably by at least 60%, still more preferably by at least 70%, more preferably by 80%, and most preferably by 90%. The ASO may comprise at least two modified nucleosides, including locked nucleic acid (LNA) units, where there the LNA unit has a 2'O-alkyl-4'C linkage, resulting in a bicyclic sugar at the position in the ASO where the modified LNA nucleoside is incorporated into the ASO sequence.

The antisense oligomer of the invention is a single stranded oligonucleotide which comprises nucleoside analogues, such as LNA, or nucleotide analogs, such as phosphorothioates, which form part of the contiguous nucleic acid sequence of the antisense oligonucleotide. The sequence of the antisense oligomer consists of a contiguous nucleotide or nucleoside sequence.

The term "antisense" as used herein, means that a nucleic acid oligonucleotide sequence, when viewed from the 5'-terminus to the 3'-terminus, comprises a sequence that is essentially complementary to the sense strand of DNA—i.e., the antisense oligonucleotide has an opposite sequence orientation, from 5'- to 3'-, as the sense strand of DNA, also known as the coding strand, so the antisense oligomer is essentially complementary to the sense strand of a given DNA coding region or gene.

The term "oligonucleotide" (or simply "oligo"), which is used interchangeably with the term "oligomer" refers, in the context of the present invention, to a molecule formed by covalent linkage of two or more nucleotides. When used in the context of the oligonucleotide of the invention (also referred to the single stranded oligonucleotide), the term "oligonucleotide" may have, in an embodiment, for example have from 10 through 26 nucleotides, more particularly an oligonucleotide of the invention may have from 12-20 nucleotides, or more particularly, from 14-18 nucleotides.

The term 'nucleotide' refers to a molecule with three components, namely a heterocyclic nitrogenous base, sometimes referred to as a nucleobase, including pyrimidine and purine bases, a pentose sugar (ribose or deoxyribose), and a phosophoryl group (phosphate, phosphorothioate, phosphonate, etc, Examples include, but are not limited to DNA nucleotides such as deoxyadenosine-5'-monophosphate (dAMP), deoxyguanosine-5'-diphosphate (dGDP), deoxylthymidine-5'-triphosphate (dTTP), and deoxycytidine-5'-triphosphate (dCTP), and RNA nucleotides such as adenine-5'-monophosphate (AMP), cytidine-5'-diphosphate (CDP), inosine-5'-monophsophate (IMP), uridine-5'-triphosphate (UTP) and guanosine-5'-triphosphate (GTP).

As used herein, nucleotide includes phosphate analogues such as phosphorothioate, phosphorodithioate, phosphonate, H-phosphonate, or alkylphosphonate analogues. It should be recognized that, in some aspects, the term nucleobase may also be used to refer to a nucleotide which may be either naturally occurring or non-naturally occurring—in this respect the term nucleobase and nucleotide may be used interchangeably herein. Nucleobases include, but are not limited to, guanine, cytosine, thymine, adenine, uracil, xanthine, hypoxanthine, 5,6-dihydrouracil, 5-fluorouracil, 5-fluorothymine, N7-methylguanine, N7-methylinosine, 5-methylcytosine, and 5-methyluracil, among others.

Oligomeric compounds provided herein may comprise one or more monomers, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a Locked Nucleic Acid (LNA).

In certain embodiments, oligomeric compounds comprise one or more monomers that is an LNA. In certain such embodiments, LNAs include, but are not limited to, (A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

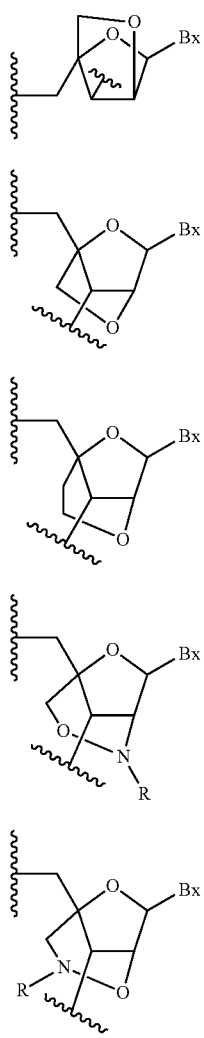

In certain embodiments, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—;

wherein:
x is 0, 1, or 2;
n is 1, 2, 3, or 4;
each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In one embodiment, each of the bridges of the LNA compounds is, independently, —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. In another embodiment, each of said bridges is, independently, 4'-CH$_2$-2', 4'-(CH$_2$)$_2$-2', (CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'- wherein each R$_1$ is, independently, H, a protecting group or C$_1$-C$_{12}$ alkyl.

Certain LNA's have been prepared and disclosed in the patent literature as well as in scientific literature (see for example: issued U.S. Pat. Nos. 7,053,207; 6,268,490; 6,770,748; 6,794,499; 7,034,133; 6,525,191; 7,696,345; 7,569,575; 7,314,923; 7,217,805; and 7,084,125, hereby incorporated by reference herein in their entirety.

Also provided herein are LNAs in which the 2'-hydroxyl group of the ribosyl sugar ring is linked to the 4' carbon atom of the sugar ring thereby forming a methyleneoxy (4'-CH$_2$—O-2') linkage to form the bicyclic sugar moiety (reviewed in Elayadi et al., *Curr. Opinion Invens. Drugs,* 2001, 2, 558-561; Braasch et al., *Chem. Biol.,* 2001, 8 1-7; and Orum et al., *Curr. Opinion Mol. Ther.,* 2001, 3, 239-243; see also U.S. Pat. No. 6,670,461). The linkage can be a methylene (—CH$_2$—) group bridging the 2' oxygen atom and the 4' carbon atom, for which the term methyleneoxy (4'-CH$_2$—O-2') LNA is used for the bicyclic moiety; in the case of an ethylene group in this position, the term ethyleneoxy (4'-CH$_2$CH$_2$—O-2') LNA is used (Singh et al., Chem. Commun., 1998, 4, 455-456: Morita et al., *Bioorganic Medicinal Chemistry,* 2003, 11, 2211-2226). Methyleneoxy (4'-CH$_2$—O-2') LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising LNAs have been described (Wahlestedt et al., *Proc. Natl. Acad. Sci. U.S.A.,* 2000, 97, 5633-5638).

An isomer of methyleneoxy (4'-CH$_2$—O-2') LNA that has also been discussed is alpha-L-methyleneoxy (4'-CH$_2$—O-2') LNA which has been shown to have superior stability against a 3'-exonuclease. The alpha-L-methyleneoxy (4'-CH$_2$—O-2') LNA's were incorporated into antisense gapmers and chimeras that showed potent antisense activity (Frieden et al., *Nucleic Acids Research,* 2003, 21, 6365-6372).

The synthesis and preparation of the methyleneoxy (4'-CH$_2$—O-2') LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226, incorporated by reference herein.

Analogs of methyleneoxy (4'-CH$_2$—O-2') LNA, phosphorothioate-methyleneoxy (4'-CH$_2$—O-2') LNA and 2'-thio-LNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-LNA, a novel comformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

In an embodiment, the antisense oligomer may comprise at least two LNA monomers, more particularly the antisense oligomer may comprise 2, 3, 4, 5, 6, 7, 8, 9 or 10 LNA monomers. As described below, the contiguous nucleotide sequence may consist of LNA and DNA units (including linkage groups, such as phosphorothioate linkages), or may consist of LNA and other nucleoside and nucleotide analogues. In some embodiments, the contiguous nucleotide sequence may comprise 6, 7, 8, 9, 10, 11, 12, 13, or 14 DNA nucleotides, the remainder of the nucleotides comprising nucleoside analogues, such as LNA units.

Certain embodiments provide ASOs from 10-100 nucleotides in length with LNA nucleotides incorporated into the sequence. Certain embodiments provide ASOs having a 4-8-4 pattern, corresponding to four LNA nucleotides, eight non-LNA gap nucleotides (nt), four LNA nucleotides, consecutively, from the 5'- to 3'-direction. Thus, a 4LNA-8 nt-4LNA motif comprises a central nucleotide (nt) gap segment having eight consecutively linked 2'-deoxynucleotides. The nt gap segment in a 4LNA-8 nt-4LNA 16-mer ASO is flanked on both sides (5' and 3') by a wing segment. Each wing segment in each ASO has four consecutively linked nucleotides. Each nucleotide of each wing segment in each ASO has a locked nucleic acid (LNA) sugar modification. Each internucleotide linkage throughout each LNA antisense oligonucleotide is a phosphorothioate (P=S) linkage, although it is envisioned that some internucleotide linkages on some ASOs of the invention may be linkages other than a phosphorothioate, including a phosphodiester linkage. It is also within the scope of the invention that the LNA motif of a given ASO may vary from 4LNA-8 nt-4LNA, to other motifs including other combinations of LNA-nt-LNA motifs of longer or shorter total nucleotide sequence. Certain embodiments provide ASOs of various other "wing-gap-wing" patterns. The "wing-gap-wing" pattern is frequently described as "X-Y-Z", where "X" represents the length of the 5' wing region, "Y" represents the length of the gap region, and "Z" represents the length of the 3' wing region. In some embodiments, X and Z are the same, in other embodiments they are different. In certain embodiments', X and Z are independently 1 to 5 nucleosides in length. In certain embodiments, Y is 8 to 12 nucleotides in length. ASOs of the invention may also be a 10-mer, 11-mer, 12-mer, 13-mer, 14-mer, 15-mer, 16-mer, 17-mer, 18-mer, 19-mer, or 20-mer (i.e. an oligomer having 10, 11, 12, 13, 14, 15, 16, 17, 18, 19, 20 nucleotides, respectively) or longer, up to 100 nucleotides in length. Other particular embodiments provide ASOs from 10 up to 100 nucleotides in length, with LNAs incorporated into the sequence in other possible alternating patterns as described above. In other particular embodiments, there may be more than one LNA-nt-LNA motif in a given sequence, such that a general formula of 5'-LNAn-P-LNAp-P-Nm-P-Nl-P-LNAr-P-LNAq-3' (formula 1), as described herein, is possible within a particular ASO from 10 through 20 nucleotides, total, in length.

In a particular embodiment, the internucleotide linkages in the antisense oligomer sequence are selected from a phosphodiester, phosphotriester, phosphorothioate, phosphorodithioate, H-phosphonate, or alkylphosphonate linkage. In a further particular embodiment, all internucleotide linkages are phosphorothioate linkages In a more particular embodiment, the internucleotide linkages in the antisense oligomer sequence are selected from phosphodiester linkages and phosphorothioate linkage.

In a more particular embodiment, the antisense oligomer comprises at least two modified nucleotides, more particularly at least two locked nucleic acid (LNA) units, where there the LNA unit has a 2'O-alkyl-4'C linkage.

A particular embodiment provides an antisense oligomer comprising at least two LNA units located towards the 3'-terminus and the 5'-terminus of the ASO, more particularly the ASO comprises at least three LNA units located towards the 3'-terminus and the 5'-terminus of the ASO, more particularly the ASO comprises at least 4 LNA units, and more particularly, the at least 4 LNA units are located towards the 3'-terminus and the 5'-terminus of the ASO, such that the ASO comprises a sequence described by formula 1 below:

$$5'\text{-LNA}_n\text{-P-LNA}_p\text{-P-N}_m\text{-P-N}_l\text{-P-LNA}_1\text{P-LNA}_q\text{-3'} \quad \text{(formula 1)}$$

wherein

LNA is a locked nucleic acid unit having a 2'-O-Me-4'C linkage;

P is selected from a phosphodiester, phosphotriester, phosphorothioate, phosphorodithioate, H-phosphonate, or alkylphosphonate linkage between a LNA and a contiguous N, or between a N and a contiguous N, or between N and a contiguous LNA, or between a LNA and a contiguous LNA, from a 5'- to 3' direction of the sequence of formula (1); and wherein N is selected from a G, C, A, T, U, or X nucleotide unit;

n and r and p and q are each independently an integer selected from 1, 2 or 3; l and m are each independently an integer from 1 through 22; and wherein X is selected from an inosine, $N^7$-methylinosine, $N^7$-methyl guanidine, 5-methyl uridine, 5-methyl-thymidine, 5-fluorouridine, 5-fluorothymidine, In a related particular embodiment, the antisense oligomer comprises at least 6 phosphorothioate linkages. In another related particular embodiment, the antisense oligomer comprises all phosphorothioate linkages In another embodiment, a method of treating an HBV infection in a mammal, including a human, is provided wherein treatment comprises administering an effective dose of an antisense oligomer of the present invention, said antisense oligomer being essentially complementary to any of SEQ ID NOs: 1-13, so as to treat the HBV infection and promote seroconversion in the mammal, including human. The effective dose may range from 0.01 mg/kg body weight, to approximately 100 mg/kg body weight, administered once or twice weekly, for 24, 36 or 48 weeks, or longer, as determined by a physician. Efficacy of treatment may be determined using quantification of viral load or other evidence of infection, such as through measurement of HBeAg, HBsAg, HBV DNA levels, ALT activity levels, serum HBV levels, and the like, thereby allowing adjustment of treatment dose, treatment frequency, and treatment length.

EXAMPLES

Preparation of Oligomers

LNA Monomer and oligonucleotide synthesis are prepared as described in published patent applications and the literature, including the methodology referred to in WO2007/112754, and the methodology described in US patent application published as US20090143326, both of which are hereby incorporated by reference herein. LNA ASOs may also be purchased from, for example, Exiqon, as described herein.

The treatment of in vitro cells with LNA antisense oligonucleotide (targeting SEQ ID NOs: 1-13 of the human HBV genome) may be performed using the methodology referred to in WO2007/112754, incorporated by reference herein, and as described herein. The analysis of antisense oligonucleotide Inhibition of HBV infection by RNA specific real time quantitative PCR in both an in vitro and in vivo model may also be performed using the methodology referred to in WO2007/112754, incorporated by reference herein, and as described herein. In addition, in vivo experiments using antisense oligomers of the invention from 10- to 100-nucleotides in length, (directed to SEQ ID NOs 1-13 of the human HBV genome) targeting HBV expression and subsequent analysis may be performed using the methods disclosed, for example, in WO2007/112754, or in J. Virol (1998) vol. 71, pp 2630-2637; or in in Yonsei Medical Journal (1995), col. 36, pp. 527-533, all of which are incorporated by reference herein. A woodchuck model for HBV has also been developed, wherein woodchucks (*Marmoto monax*) can be infected with Woodchuck Hepatitis Virus (WHV) resulting in chronic or acute infections that model many aspects of human HBV infection [Menne S and Cote P J (2007) World J Gastroenterol 13, 104-124 and Menne S et al (2002) Intervirology 45, 237-250] incorporated by reference herein. The woodchuck model, described by Menne and Cote and Menne et. al, can be used to examine chronic infection and to measure viral DNA in the serum using blot Southern hybridization and measure viral antigens in serum by ELISA.

Biological Activity (A) Human Hepatitis B Results

Example 1

Antisense Inhibition of Hepatitis B Virus Expression in HepG2 2.2.15 Cells with LNA Antisense Oligonucleotides Locked nucleic acid oligonucleotides were purchased from Exiqon. The LNA antisense oligonucleotides tested were 16 nucleotides in total length, with each having a 4LNA-8 nt-4LNA motif, and each comprising a central nucleotide (nt) gap segment having eight consecutively linked 2'-deoxynucleotides. The nt gap segment in each 16-mer ASO is flanked on both sides (5' and 3') by a wing segment. Each wing segment in each ASO has four consecutively linked nucleotides. Each nucleotide of each wing segment in each ASO has a locked nucleic acid (LNA) sugar modification. Each internucleotide linkage throughout each LNA antisense oligonucleotide is a phosphorothioate (P=S) linkage, although it is envisioned that some internucleotide linkages on some ASOs of the invention may be linkages other than a phosphorothioate, including a phosphodiester linkage. It is also within the scope of the invention that the LNA motif of a given ASO may vary from 4LNA-8 nt-4LNA, to other motifs as described herein including other combinations of LNA-nt-LNA motifs of longer or shorter total nucleotide sequence. The 16-mer LNA ASOs were evaluated for the ability to inhibit hepatitis B virus expression in a human hepatoblastoma cell line, HepG2.2.15, as determined by measuring levels of HBsAg, HBeAg, and HBV DNA.

All oligonucleotides contained phosphorothioate linkages, were 16 nucleotides in length and contained locked nucleic acids in a 4-8-4 motif, comprising LNAs at the 4 nucleotides at the 5'-ends and at the 4 nucleotides at the 3'-ends. The sequences of the antisense oligonucleotides, (incorporated by reference herein as SEQ ID NOs 14-23), are presented in Table 1.

TABLE 1

Antisense Oligonucleotides

| Name | Sequence | HBV target sequence Accession U95551 | $IC_{50}$ Values (nM) | | | HBV DNA Inhibition at 0.6 nM |
|---|---|---|---|---|---|---|
| | | | HBsAg | HBeAg | cytotox | |
| RH1 (SEQ ID NO: 14) | GAGAGAAGTCCACCAC | nt 258-273 | 1.31 | 1.35 | 23.6 | 34% |
| RH2 (SEQ ID NO: 15) | TGAGAGAAGTCCACCA | nt 259-274 | 1.06 | 0.97 | 8.7 | -21% |
| RH3 (SEQ ID NO: 16) | GAGGCATAGCAGCAGG | nt 414-429 | 1.10 | 1.16 | 39.3 | 26% |
| RH4 (SEQ ID NO: 17) | TGAGGCATAGCAGCAG | nt 415-430 | 1.04 | 0.97 | 19.9 | 34% |
| RH5 (SEQ ID NO: 18) | GATGAGGCATAGCAGC | nt 417-432 | 0.92 | 0.88 | 9.8 | 26% |
| RH6 (SEQ ID NO: 19) | GATGGGATGGGAATAC | nt 602-617 | 1.46 | 0.62 | 14.3 | 30% |

TABLE 1-continued

Antisense Oligonucleotides

| Name | Sequence | HBV target sequence Accession U95551 | IC$_{50}$ Values (nM) HBsAg | HBeAg | cytotox | HBV DNA Inhibition at 0.6 nM |
|---|---|---|---|---|---|---|
| RH7 (SEQ ID NO: 20) | GGCCCACTCCCATAGG | nt 639-654 | 0.90 | 0.49 | 22.4 | 40% |
| RH8 (SEQ ID NO: 21) | AGGCCCACTCCCATAG | nt 640-655 | 1.84 | 1.27 | 9.0 | -40% |
| RH9 (SEQ ID NO: 22) | CTGAGGCCCACTCCCA | nt 643-658 | 1.13 | 0.91 | 8.1 | 22% |
| Control (SEQ ID NO: 23) | GTGTAACACGTCTATA | | 5.04 | 5.77 | 17.8 | -51% |

Monolayers of HepG2 2.2.15 cells, a human hepatoblastoma cell line, stably transfected with a plasmid having head-to-tail dimmers of HBV gene, were grown in RPMI (Invitrogen #22400-089), 10% FBS, gentamicin (10 µg/ml) at 37° C., 5% $CO_2$ and were split 1:3 when confluent.

Stock solutions of antisense oligonucleotides were prepared in sterile water and were diluted to a concentration of 4.25 µM for transfection. 10 µL of oligonucleotide was mixed with 130 µL of Opti-Mem (Invitrogen). 100 µL of the oligonucleotide mixture was mixed with 100 µL Lipofectamine 2000 (Invitrogen) and incubated for 20 minutes at room temperature. Serial dilutions were performed by diluting 70 µL into 140 µL of Opti-Mem. 50 µL of the diluted mixture was added to a 96-well plate and 100 µL of HepG2 2.2.15 cells at a concentration of $2.8 \times 10^5$/mL was added. The transfected cells were incubated at 37° C., 5% $CO_2$ for 4 days with a media change on day 2. The supernatant was removed on day 4 for evaluation of secreted HBsAg, HBeAg, and HBV DNA and cell viability was determined on the remaining cell monolayer using CellTiter-Glo (Promega) according to the manufacturer's instructions. HBsAg levels were measured using the Abazyme HBV s Ag kit, catalog #EL10018, according to the manufacturer's instructions. HBeAg levels were measured using the BioChain HBV e Ag kit, catalog #KO31006096 according to the manufacturer's instructions.

For analysis of HBV DNA in the supernatant, DNA was extracted from 50 µL of supernatant using the QiaAmp 96 DNA Blood Kit (Qiagen) according to the manufacturer's instructions. 5 µL of DNA was used for TaqMan analysis using primers and conditions as described [Thimme R et al (2003) J. Virol. 77, 68-76]. A standard curve based on known quantities of a plasmid clone of HBV DNA was used to calculate HBV genome equivalents secreted in the media.

Inhibition of cell viability, HBV DNA, and secreted antigens were normalized using values from cells undergoing the transfection procedure in the absence of oligonucleotide. Data were analyzed by non-linear regression and fit to a log(inhibitor) vs response curve using GraphPad Prism5.

The results of treatment of HepG2 2.2.15 cells with antisense oligomers is shown in Table 1. All of the antisense oligomers directed against HBV sequences inhibited the production and secretion of HBsAg and HBeAg with a potency greater than that of the control oligomer. The control oligomer also inhibited the production and secretion of antigen but this may be due to cytotoxicity as there was only a 3-fold difference between the 1050 values for antigen inhibition and cytotoxicity. The antisense oligomers directed against HBV sequences had a greater fold difference between the IC50 values for antigen inhibition and cytotoxicity. Antisense oligomers RH1, RH3, RH4, and RH7 had the greatest fold differences and showed consistent inhibition of secreted HBV DNA as well. Inhibition of HBV DNA did not increase above 50% so 1050 values were not calculated. Shown in Table 1 are the % inhibition of HBV DNA at a concentration of 0.6 nM oligomer, a concentration where no cytotoxicity was observed for any oligomer and close to the 1050 values for inhibition of HBsAg and HBeAg.

Example 2

Antisense Inhibition of Hepatitis B Virus or SV40 T Antigen Expression in HepAD38 (Tet-HBV) Cells with an LNA Antisense Oligonucleotide An LNA antisense oligonucleotide targeting HBV was designed with the sequence GAGGCATAGCAGCAGG (SEQ ID NO: 16), complementary to the DNA sequence recited in SEQ ID NO: 4 and GENBANK Accession No. U95551.1, incorporated herein as SEQ ID NO: 16. The LNA antisense oligonucleotide is 16 nucleotides in total length, with a 4-8-4 LNA motif, wherein the ASO has a central gap segment having eight consecutively linked 2'-deoxynucleotides. The gap segment is flanked on both sides (5' and 3') by a wing segment. Each wing segment has four consecutively linked nucleotides. Each nucleotide of each wing segment has a locked nucleic acid (LNA) sugar modification. Each internucleotide linkage throughout the LNA antisense oligonucleotide is a phosphorothioate (P=S) linkage. Each cytosine of the LNA antisense oligonucleotide is a 5-methylcytosine. The LNA antisense oligonucleotide was evaluated for its ability to reduce HBV mRNA in HepAD38 cells.

HepAD38 cells were transfected using electroporation with 741 nM, 2,222 nM, 6,667 nM, and 20,000 nM of antisense oligonucleotides for a period of approximately 24 hours. RNA was isolated from the cells and HBV mRNA levels were measured by quantitative real-time PCR. HBV mRNA levels were adjusted according to total RNA content as measured by RIBOGREEN. Primer probe set RTS3372 (forward sequence ATCCTATCAACACTTCCGGAAACT, designated herein as SEQ ID NO: 24; reverse sequence CGACGCGGCGATTGAG, designated herein as SEQ ID NO: 25, probe sequence AAGAACTCCCTCGCCTCGCA-GACG, designated herein as SEQ ID NO: 26) was used to measure mRNA levels. The data is presented in Table 2, expressed as percent inhibition of mRNA levels compared to untreated cells. The LNA antisense oligonucleotide reduced HBV mRNA levels in a dose-dependent manner.

The LNA antisense oligonucleotide was also tested under the same conditions with primer probe set RTS3373MGB (forward sequence CCGACCTTGAGGCATACTTCA, designated herein as SEQ ID NO: 27; reverse sequence AATT-TATGCCTACAGCCTCCTAGTACA, designated herein as SEQ ID NO: 28, probe sequence TTAAAGACTGGGAG-GAGTTG, designated herein as SEQ ID NO: 29). The results are presented in Table 3 as percent inhibition of HBV, relative to untreated control cells. As illustrated in Table 3, the LNA antisense oligonucleotide reduced HBV mRNA levels in a dose-dependent manner.

TABLE 2

Dose-dependent antisense inhibition of HBV mRNA in HepAD38 cells, as measured with RTS3372

| Dose (nM) | % inhibition |
|---|---|
| 741 | 0 |
| 2222 | 30 |
| 6667 | 54 |
| 20000 | 72 |

TABLE 3

Dose-dependent antisense inhibition of HBV mRNA in HepAD38 cells, as measured with RTS3373MGB

| Dose (nM) | % inhibition |
|---|---|
| 741 | 0 |
| 2222 | 7 |
| 6667 | 9 |
| 20000 | 50 |

Example 3

Antisense Inhibition of Hepatitis B Virus or SV40 T Antigen Expression in Expression in THT1 Cells with an LNA Antisense Oligonucleotide The LNA antisense oligonucleotide described in Example 3 was evaluated for its ability to reduce HBV mRNA in THT1 cells, also known as HepG2 2.2.15 cells. These cells were transfected using electroporation with 741 nM, 2,222 nM, 6,667 nM, and 20,000 nM of antisense oligonucleotides for a period of approximately 24 hours. RNA was isolated from the cells and HBV mRNA levels were measured by quantitative real-time PCR. HBV mRNA levels were adjusted according to total RNA content as measured by RIBOGREEN. The data is presented in Table 4, expressed as percent inhibition of mRNA levels compared to untreated cells. As illustrated in Table 4, the LNA antisense oligonucleotide reduced HBV mRNA levels in a dose-dependent manner.

TABLE 4

Dose-dependent antisense inhibition of HBV mRNA in HepG2 cells

| Dose (nM) | % inhibition |
|---|---|
| 741 | 34 |
| 2222 | 38 |
| 6667 | 42 |
| 20000 | 57 |

(B) Assessment of Antisense Oligomers in Animal Models

Example 4

Assessment of ASO Effectiveness in Reducing HBV Load in Transgenic Mice

An HBV transgenic mouse lineage 1.3.32 (official designation, Tg[HBV 1.3 genome]Chi32) is used to assess antisense oligomer effectiveness in reducing HBV load in an animal model. The transgenic mice replicate HBV at high levels in the liver and kidney without any evidence of cytopathology. Lineage 1.3.32 is expanded by repetitive back-crossing against the C57BL/6 parental strain and then bred one generation against B10D2 mice to produce the F1 hybrids to be used in all the assays described. Mice are matched for age (6 to 10 weeks), sex (male), and levels of hepatitis B surface antigen (HBsAg) in the serum (determined by using a commercially available kit from Abbott Laboratories, Abbott Park, Ill.).

(A) HBV transgenic mice are treated with HBV DNA oligomers for 7-21 days by intravenous or subcutaneous administration, and then sacrificed. Mouse liver is then analyzed for reduction in HBV DNA and RNA levels. Southern blot methods or Real Time QPCR are used to determine DNA levels, Northern blot methods or Real Time QPCR methods are used to determine HBV RNA transcript levels. Mouse serum is also analyzed for production levels of HBeAg and HBsAg using commercially available ELISA kits for HBeAg and HBsAg.

The DNA is analyzed by Southern blots and probed with $^{32}$P-labelled HBV DNA probe in accordance with the following procedure. The DNA from HBV-infected hepatocytes is extracted, separated by electrophoresis in agarose gels and transferred onto a nitrocellulose filter using methodologies common to those skilled in the art. A $^{32}$P-nick translated-HBV DNA probe is used. In the viral control group, livers are harvested at 2, 6, 8, 10, 14, 18 and 20 days. In drug-treated groups, livers are harvested on days 8, 14 and 20. Liver samples are ground with a well-fitted pestle in a microcentrifuge tube containing lysis buffer. After incubation for 5-10 min at room temperature, the tubes are snap-frozen in liquid nitrogen for storage. DNA is purified using phenol/chloroform extraction and ethanol precipitation. Liver DNA cut with Hind III, which did not cut within the transgene, is fractionated by agarose gel electrophoresis and then processed for Southern blot hybridization using the alkaline transfer method with nitrocellulose or other appropriate membrane.

The RNA is analyzed by Northern blots and probed with $^{32}$P-labelled HBV DNA probe in accordance with the following procedure. Liver samples are processed for RNA extraction using Trizol reagent per the manufacturer's protocol.

Briefly, tissue samples are homogenized in 1 ml of TRIZOL reagent per 50 to 100 mg of tissue using a glass-Teflon or power homogenizer (e.g. Polytron, Tekmar's TISSUEM-IZER). Incubate the homogenized sample for 5 minutes at room temperature and then centrifuge to remove cell debris. Transfer the supernatant to new tube. Add 0.2 ml of chloroform per 1 ml of TRIZOL Reagent. Cap sample tubes securely. Vortex samples vigorously for 15 seconds and incubate them at room temperature for 2 to 3 minutes. Centrifuge the samples at no more than 12,000×g for 15 minutes at 2 to 8° C. Transfer upper aqueous phase carefully without disturbing the interphase into fresh tube. Measure the volume of the aqueous phase (The volume of the aqueous phase is about 60% of the volume of TRIZOL Reagent used for homogenization). Precipitate the RNA from the aqueous phase by mixing with isopropyl alcohol. Use 0.5 ml of isopropyl alcohol per 1 ml of TRIZOL Reagent used for the initial homogenization. Incubate samples at 15 to 30° C. for 10 minutes and centrifuge at not more than 12,000×g for 10 minutes at 2 to 4° C. The RNA precipitate, often invisible before centrifugation, forms a gel-like pellet on the side and bottom of the tube. Remove the supernatant completely. Wash the RNA pellet once with 75% ethanol, adding at least 1 ml of 75% ethanol per 1 ml of TRIZOL Reagent used for the initial homogenization. Mix the samples by vortexing and centrifuge at no more than 7,500×g for 5 minutes at 2 to 8° C. Repeat above washing procedure once. Remove all leftover ethanol. Air-dry or vacuum dry RNA pellet for 5-10 minutes. Dissolve RNA in DEPC-treated water by passing solution a few times through a pipette tip. RNA is resolved in formaldehyde agarose gels and transferred to nitrocellulose or other appropriate membrane. A $^{32}$P-nick translated-HBV DNA probe is used to detect HBV transcripts.

The drugs tested are scored on a scale of 0 (no activity) to ++++ (high activity).

Example 5

Assessment of Antisense Oligomers Using Woodchucks Infected with WHV

Woodchucks (*Marmoto monax*) can be infected with Woodchuck Hepatitis Virus (WHV) resulting in chronic or acute infections that model many aspects of human HBV infection [Menne S and Cote P J (2007) World J Gastroenterol 13, 104-124]. Chronic infection can be established by infection of neonates with WHV7P1. Viral DNA in the serum can be measured by dot blot Southern hybridization and viral antigens in serum by ELISA [Menne S et al (2002) Intervirology 45, 237-250].

The DNA sequence of WHV differs from HBV so antisense oligomers will need to be optimized for WHV. An in vitro system exists for this purpose that has been used previously for evaluation of siRNA [Meng Z et al (2009) Virology 384, 88-96].

Woodchucks chronically infected with WHV are treated with antisense oligomers by intravenous or subcutaneous administration. The dosing regimen will be dependent upon the previous determination of the intrahepatic half-life of the antisense oligomer in woodchucks but will be once or twice weekly. The treatment duration will be for 6 months. Serum levels of viral DNA, viral antigens, and antibodies to viral antigens will be measured periodically during treatment and for at least 3 months post-treatment. Reductions in viral DNA and viral antigens sustained throughout the follow-up period are indicative of a positive outcome. Prolonged treatment of woodchucks chronically infected with WHV by potent nucleoside analogs results in viral recrudescence within 1-2 months of treatment cessation. Reductions in WHV DNA and seroconversion, defined as loss of viral antigen and occurrence of antibody to the antigen, are also indicative of a positive treatment outcome.

The antisense oligonucleotide compounds intended for testing in HBV infected patients are essentially complementary to any one of SEQ:ID NOs: 1-13, shown below. These sequences are conserved across more than 95% of HBV human geographical genotypes A through H, listed in FIG. 6.

For humans, the treatment regimen is typically 48 weeks, similar to that used for Peg-IFN (weekly SC injection for 48 weeks), but with no INF-like systemic side effects expected, based on similar therapy carried out using LNA antisense oligomers for treating hepatitis C virus (HCV), where no systemic side effect were observed (unpublished results). Expected results include reduction in HBV DNA and serum antigens, HBeAg seroconversion greater than that seen with treatment using Peg-IFN in HBeAg positive patients, and undetectable HBV DNA and/or HBsAg seroconversion greater than that seen with treatment using Peg-IFN in HBeAg negative patients.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An antisense compound comprising a single-stranded modified antisense oligonucleotide consisting of 16 nucleotides having a contiguous nucleoside sequence, wherein nucleotides in the oligonucleotide are connected by internucleotide linkages and wherein the nucleoside sequence is selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22 wherein at least one nucleotide comprises a modified sugar.

2. An antisense compound according to claim 1 wherein the modified sugar is a LNA having a chemical link between a 2'- and 4'-atom of the nucleotide sugar.

3. An antisense compound according to claim 1 wherein the internucleotide linkages are selected from the group consisting of a phosphodiester, phosphotriester, phosphorothioate, phosphorodithioate, H-phosphonate, or alkylphosphonate linkage.

4. An antisense compound according to claim 2, wherein the chemical link is a 2'O-alkyl-4'C chemical link and wherein the alkyl is optionally substituted or non-substituted.

5. An antisense compound according to claim 1, wherein the nucleoside sequence is further selected from the group consisting of SEQ ID NO: 14, SEQ ID NO: 16, SEQ ID NO: 17, and SEQ ID NO: 20.

6. An antisense compound comprising a single-stranded modified antisense oligonucleotide consisting of 16 nucleotides having a contiguous nucleoside sequence wherein nucleotides in the oligonucleotide are connected by internucleotide linkages, and wherein the nucleoside sequence is essentially complementary to a sequence selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; and SEQ ID NO: 13.

7. An antisense compound according to claim 6 comprising at least one modified nucleotide that is a LNA.

8. An antisense compound according to claim 7 wherein the internucleotide linkages are selected from the group consisting of a phosphodiester, phosphotriester, phosphorothioate, phosphorodithioate, H-phosphonate, or alkylphosphonate linkage.

9. A pharmaceutical formulation for treating hepatitis B virus infection in a mammal comprising an effective amount of a compound according to claim 1, or a pharmaceutically acceptable salt, solvate, hydrate or ester thereof, and a pharmaceutically acceptable diluent.

10. A pharmaceutical formulation for treating hepatitis B virus in a mammal comprising an effective amount of a compound according to claim 6, or a pharmaceutically acceptable salt, solvate, hydrate or ester thereof, and a pharmaceutically acceptable diluent.

11. A pharmaceutical formulation for treating hepatitis B virus infection in a mammal according to claim 10, further comprising a pharmaceutically acceptable carrier.

12. A method for treating a mammal having a hepatitis B virus infection or a hepatitis B virus-related condition, the method comprising administering a therapeutically effective amount of a compound according to claim 1 to a mammal in need thereof so as to treat the hepatitis B virus infection, or the hepatitis B virus-related condition.

13. A method according to claim 12, wherein the mammal is a human, wherein the hepatitis B virus infection or the hepatitis B virus-related condition is a hepatitis B virus infection from a human hepatitis B virus.

14. A method for treating a mammal having a hepatitis B virus infection according to claim 12, wherein the human hepatitis B virus is selected from any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

15. A method according to claim 12, wherein the mammal is a human, and wherein the hepatitis B virus infection or the hepatitis B virus-related condition is a human hepatitis B virus-related condition.

16. A method according to claim 13, wherein the human hepatitis B virus-related condition is selected from any of: jaundice, liver cancer, liver inflammation, liver fibrosis, liver cirrhosis, liver failure, diffuse hepatocellular inflammatory disease, hemophagocytic syndrome or serum hepatitis.

17. A method according to claim 12, further comprising administering the compound in combination with an additional therapeutic agent, wherein the antisense oligomer and the additional therapeutic agent are administered either together in a single formulation, or administered in separately in different formulations, and wherein the administration of the nucleic acid oligomer and the second therapeutic agent is done concomitantly, or in series.

18. A method according to claim 17, wherein the additional therapeutic agent is selected from an HBV agent, an HCV agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, and an immunosuppressant agent.

19. A method according to claim 18, wherein the additional HBV agent is selected from interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir; tenofovir; telbivudine (LdT); adefovir; and an HBV antibody therapy (monoclonal or polyclonal).

20. A method according to claim 18, wherein the additional HCV agent is selected from interferon alpha-2b, interferon alpha-2a, and interferon alphacon-1 (pegylated and unpegylated); ribavirin; an HCV RNA replication inhibitor; an HCV antisense agent; an HCV therapeutic vaccine; an HCV protease inhibitor; an HCV helicase inhibitor; and an HCV monoclonal or polyclonal antibody therapy.

21. A method for reducing a presence of HBV antigen in a mammal infected with a hepatitis B virus, the method comprising administering a therapeutically effective amount of a compound according to claim 1 to a mammal in need thereof so as to reduce the hepatitis B antigen, compared to the presence of HBV antigen in the mammal before treatment.

22. A method according to claim 21, wherein the mammal is a human, and wherein the hepatitis B virus is a human hepatitis B virus.

23. A method according to claim 21, wherein the human hepatitis B virus is selected from any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

24. A method according to claim 21, wherein the HBV antigen is HBsAg.

25. A method according to claim 21, wherein the HBV antigen is HBeAg.

26. A method according to claim 21, wherein the presence of HBV antigen is sufficiently reduced to result in seroconversion, defined as serum HBeAg absence plus serum HBeAb presence if monitoring HBeAg as the determinant for seroconversion, or defined as serum HBsAg absence if monitoring HBsAg as the determinant for seroconversion, as determined by currently available detection limits of commercial ELISA systems.

27. A method according to claim 21, further comprising administering the compound in combination with an additional therapeutic agent, wherein the antisense oligomer and the additional therapeutic agent are administered either together in a single formulation, or administered in separately in different formulations, and wherein the administration of the nucleic acid oligomer and the second therapeutic agent is done concomitantly, or in series.

28. A method according to claim 27, wherein the additional therapeutic agent is selected from an HBV agent, an HCV agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, and an immunosuppressant agent.

29. A method according to claim 27, wherein the additional HBV agent is selected from interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir; tenofovir; telbivudine (LdT); adefovir; and an HBV antibody therapy (monoclonal or polyclonal).

30. A method according to claim 28, wherein the additional HCV agent is selected from interferon alpha-2b, interferon alpha-2a, and interferon alphacon-1 (pegylated and unpegylated); ribavirin; an HCV RNA replication inhibitor an HCV antisense agent; an HCV therapeutic vaccine; an HCV protease inhibitor; an HCV helicase inhibitor; and an HCV monoclonal or polyclonal antibody therapy.

31. A method for promoting seroconversion in a mammal infected with a hepatitis B virus, the method comprising:
    administering a therapeutically effective amount of a compound according to claim 1 or a pharmaceutical composition
according to claim 13 to a mammal infected with hepatitis B virus;
    monitoring for presence of HBeAg plus HBeAb in a serum sample of the mammal; or
    monitoring for presence of HBsAg in a serum sample of the mammal, such that the absence of HBeAg plus the presence of HBeAb in the serum sample if monitoring HBeAg as the determinant for seroconversion, or the absence of HBsAg in the serum sample if monitoring HBsAg as the determinant for seroconversion, as determined by currently available detection limits of commercial ELISA systems, is indication of seroconversion in the mammal.

32. A method according to claim 12, wherein administration is selected from oral, buccal, rectal, parenteral, intraperitoneal, intradermal, transdermal or intratracheal administration.

33. The compound of claim 1 wherein at least one nucleoside comprises a modified nucleobase.

34. A method for reducing an amount of HBV DNA in a mammal infected with a hepatitis B virus, the method comprising administering a therapeutically effective amount of a compound according to claim 1 to a mammal in need thereof so as to reduce the amount of HBV DNA in the mammal infected with the hepatitis B virus, compared to the amount of HBV DNA in the mammal before treatment.

35. A method according to claim 34, wherein the amount of DNA is reduced 90% compared to amount before administration of the compound.

* * * * *

UNITED STATES PATENT AND TRADEMARK OFFICE
CERTIFICATE OF CORRECTION

PATENT NO. : 8,598,334 B2  
APPLICATION NO. : 13/502370  
DATED : December 3, 2013  
INVENTOR(S) : Hamatake et al.

It is certified that error appears in the above-identified patent and that said Letters Patent is hereby corrected as shown below:

Title Page, Item (12) "Hamatake" should read -- Hamatake, et al. --.

Title Page, Item (75) Inventor is corrected to read:
-- Robert K. Hamatake, Durham (NC);
Zhi Hong, Durham (NC) --.

Signed and Sealed this
Twenty-seventh Day of October, 2015

Michelle K. Lee
*Director of the United States Patent and Trademark Office*

SEQUENCE LISTING

<160> NUMBER OF SEQ ID NOS: 29

<210> SEQ ID NO 1
<211> LENGTH: 20
<212> TYPE: DNA
<213> ORGANISM: Hepatitis B virus

<400> SEQUENCE: 1
cctgctggtg gctccagttc                                              20

<210> SEQ ID NO 2
<211> LENGTH: 42
<212> TYPE: DNA
<213> ORGANISM: Hepatitis B virus -continued

```
<400> SEQUENCE: 2
agagtctaga ctcgtggtgg acttctctca attttctagg gg                          42

<210> SEQ ID NO 3
<211> LENGTH: 26
<212> TYPE: DNA
<213> ORGANISM: Hepatitis B virus

<400> SEQUENCE: 3
tggatgtgtc tgcggcgttt tatcat                                            26

<210> SEQ ID NO 4
<211> LENGTH: 27
<212> TYPE: DNA
<213> ORGANISM: Hepatitis B virus

<400> SEQUENCE: 4
catcctgctg ctatgcctca tcttctt                                           27

<210> SEQ ID NO 5
<211> LENGTH: 17
<212> TYPE: DNA
<213> ORGANISM: Hepatitis B virus

<400> SEQUENCE: 5
caaggtatgt tgcccgt                                                      17

<210> SEQ ID NO 6
<211> LENGTH: 17
<212> TYPE: DNA
<213> ORGANISM: Hepatitis B virus

<400> SEQUENCE: 6
tgtattccca tcccatc                                                      17

<210> SEQ ID NO 7
<211> LENGTH: 20
<212> TYPE: DNA
<213> ORGANISM: Hepatitis B virus

<400> SEQUENCE: 7
cctatgggag tgggcctcag                                                   20

<210> SEQ ID NO 8
<211> LENGTH: 19
<212> TYPE: DNA
<213> ORGANISM: Hepatitis B virus

<400> SEQUENCE: 8
tggctcagtt tactagtgc                                                    19

<210> SEQ ID NO 9
<211> LENGTH: 17
<212> TYPE: DNA
<213> ORGANISM: Hepatitis B virus

<400> SEQUENCE: 9
gggctttccc ccactgt                                                      17

<210> SEQ ID NO 10
<211> LENGTH: 30
<212> TYPE: DNA
<213> ORGANISM: Hepatitis B virus
```

```
<400> SEQUENCE: 10
tcctctgccg atccatactg cggaactcct                                      30

<210> SEQ ID NO 11
<211> LENGTH: 19
<212> TYPE: DNA
<213> ORGANISM: Hepatitis B virus

<400> SEQUENCE: 11
cgcacctctc tttacgcgg                                                  19

<210> SEQ ID NO 12
<211> LENGTH: 17
<212> TYPE: DNA
<213> ORGANISM: Hepatitis B virus

<400> SEQUENCE: 12
ggagtgtgga ttcgcac                                                    17

<210> SEQ ID NO 13
<211> LENGTH: 20
<212> TYPE: DNA
<213> ORGANISM: Hepatitis B virus

<400> SEQUENCE: 13
gaagaagaac tccctcgcct                                                 20

<210> SEQ ID NO 14
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 14
gagagaagtc caccac                                                     16

<210> SEQ ID NO 15
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 15
tgagagaagt ccacca                                                     16

<210> SEQ ID NO 16
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 16
gaggcatagc agcagg                                                     16

<210> SEQ ID NO 17
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 17
```
tgaggcatag cagcag                                                     16

<210> SEQ ID NO 18
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 18
gatgaggcat agcagc                                                     16

<210> SEQ ID NO 19
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 19
gatgggatgg gaatac                                                     16

<210> SEQ ID NO 20
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 20
ggcccactcc catagg                                                     16

<210> SEQ ID NO 21
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 21
aggcccactc ccatag                                                     16

<210> SEQ ID NO 22
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 22
ctgaggccca ctccca                                                     16

<210> SEQ ID NO 23
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 23
gtgtaacacg tctata                                                     16

<210> SEQ ID NO 24
<211> LENGTH: 24
<212> TYPE: DNA
<213> ORGANISM: Artificial Sequence
<220> FEATURE:

-continued

```
<223> OTHER INFORMATION: primer

<400> SEQUENCE: 24
atcctatcaa cacttccgga aact                                          24

<210> SEQ ID NO 25
<211> LENGTH: 16
<212> TYPE: DNA
<213> ORGANISM: Artificial Sequence
<220> FEATURE:
<223> OTHER INFORMATION: primer

<400> SEQUENCE: 25
cgacgcggcg attgag                                                   16

<210> SEQ ID NO 26
<211> LENGTH: 24
<212> TYPE: DNA
<213> ORGANISM: Artificial Sequence
<220> FEATURE:
<223> OTHER INFORMATION: probe

<400> SEQUENCE: 26
aagaactccc tcgcctcgca gacg                                          24

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
ccgaccttga ggcatacttc a                                             21

<210> SEQ ID NO 28
<211> LENGTH: 27
<212> TYPE: DNA
<213> ORGANISM: Artificial Sequence
<220> FEATURE:
<223> OTHER INFORMATION: primer

<400> SEQUENCE: 28
aatttatgcc tacagcctcc tagtaca                                       27

<210> SEQ ID NO 29
<211> LENGTH: 20
<212> TYPE: DNA
<213> ORGANISM: Artificial Sequence
<220> FEATURE:
<223> OTHER INFORMATION: probe

<400> SEQUENCE: 29
ttaaagactg ggaggagttg                                               20
```